(12) United States Patent
Baker et al.

(10) Patent No.: US 8,916,542 B2
(45) Date of Patent: *Dec. 23, 2014

(54) CHITOSAN DERIVATIVES, COMPOSITIONS AND RELATED METHODS OF USE

(75) Inventors: Shenda Baker, Upland, CA (US); William P. Wiesmann, Washington, DC (US); Stacy Townsend, Claremont, CA (US)

(73) Assignee: Synedgen, Inc., Claremont, CA (US)

( * ) Notice: Subject to any disclaimer, the term of this patent is extended or adjusted under 35 U.S.C. 154(b) by 284 days.

This patent is subject to a terminal disclaimer.

(21) Appl. No.: 12/617,716

(22) Filed: Nov. 12, 2009

(65) Prior Publication Data

US 2010/0130443 A1      May 27, 2010

Related U.S. Application Data

(60) Provisional application No. 61/113,904, filed on Nov. 12, 2008, provisional application No. 61/113,982, filed on Nov. 12, 2008, provisional application No. 61/113,983, filed on Nov. 12, 2008.

(51) Int. Cl.
  *A61K 31/722*   (2006.01)
  *C07H 1/00*   (2006.01)
  *C12N 1/20*   (2006.01)

(52) U.S. Cl.
  CPC .................................... *A61K 31/722* (2013.01)
  USPC ......................... 514/55; 536/123.1; 435/252.1

(58) Field of Classification Search
  USPC ........................ 514/55, 55.1, 55.2; 536/123.1; 435/252.1
  See application file for complete search history.

(56) References Cited

U.S. PATENT DOCUMENTS

| 4,946,870 | A  | * | 8/1990 | Partain et al. .................. 514/777 |
| 6,306,835 | B1 | * | 10/2001 | Daly et al. ....................... 514/55 |
| 6,316,007 | B1 |   | 11/2001 | Nordquist et al. |
| 2007/0281904 | A1 | * | 12/2007 | Baker et al. ...................... 514/55 |

FOREIGN PATENT DOCUMENTS

WO       WO 00/12048       *   3/2000

OTHER PUBLICATIONS

Merck Manual, 1992, 16th Edn, pp. 86-88, 100-104.*
Hu et al, J. Appl. Polym. Sci., 2002, 86, 2877-2983.*
International Search Report and Written Opinion in corresponding International Application PCT/US2009/064284, 11 pgs., dated Jan. 20, 2010.

* cited by examiner

*Primary Examiner* — Ganapathy Krishnan
(74) *Attorney, Agent, or Firm* — Lando & Anastasi LLP

(57) ABSTRACT

Described herein are methods and compositions using chitosan derivatives to treat and/or inhibit acquisition of multiple drug resistance (MDR). Also described herein are methods and compositions using chitosan derivatives in combination with an antibacterial agent to treat a bacterial infection and/or inhibit growth of bacteria, for example, resulting in a synergistic or sensitizing effect.

15 Claims, 8 Drawing Sheets

CHITOSAN DERIVATIVES, COMPOSITIONS AND RELATED METHODS OF USE

PRIORITY CLAIM

The present application claims the benefit of U.S. provisional application Nos. 61/113,904, 61/113,982 and 61/113,983, all of which were filed on Nov. 12, 2008. The contents of the aforementioned applications are incorporated herein by reference in their entirety.

FIELD OF THE INVENTION

The invention relates to the soluble chitosans or chitosan derivatives, compositions comprising soluble chitosans or chitosan derivatives, and uses thereof.

BACKGROUND

Anti-bacterial agents represent one of the most important advances in the history of medicine. Several factors have emerged however, which limit the contribution of anti-bacterials including the rise of resistant strains (e.g., strains harboring vectors which confer MDR) and the reluctance of medical practitioners to overuse existing anti-bacterial agents.

SUMMARY OF THE INVENTION

Applicants have discovered novel uses for soluble chitosans or chitosan derivatives. For example, the soluble chitosans or chitosan derivatives described herein can be used to treat and/or inhibit acquisition of multiple drug resistance (MDR). The soluble chitosans or chitosan derivatives described herein can also be used in combination with an antibacterial agent, for example treat a bacterial infection and/or inhibit growth of bacteria.

The derivatized chitosans described herein can be used to treat a subject having a multiple drug resistant (MDR) bacterial infection.

In one aspect, the invention features a method of inhibiting the transfer of MDR by an MDR bacterium, or acquisition of MDR by a non-MDR bacterium, comprising:

contacting a bacterium harboring a vector which confers MDR with an effective amount of a derivatized chitosan, thereby inhibiting the transfer of MDR by an MDR bacterium, or acquisition of MDR by a non-MDR bacterium.

In some embodiments, the inhibition is in vivo, in the body of a subject.

In some embodiments, the inhibition is in vitro or ex vivo, or otherwise not in the body of a subject.

In some embodiments, the MDR bacterium is identified as an MDR strain before, at the time of, or after said contact.

In some embodiments, the derivatized chitosan is soluble at physiological pH, e.g., from about 6.8 to about 7.4.

In some embodiments, the derivatized chitosan is soluble in aqueous solution from about pH 3 to about pH 9.

In some embodiments, the derivatized chitosan comprises a chitosan of the following formula (I):

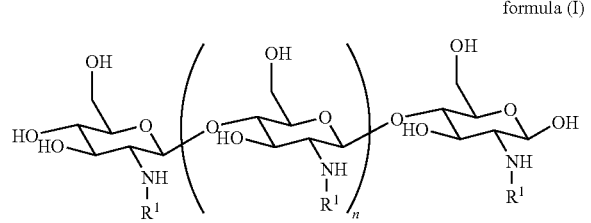

formula (I)

wherein:

n is an integer between 20 and 6000; and each $R^1$ is independently selected for each occurrence from hydrogen, acetyl, and either:

a) a group of formula (II):

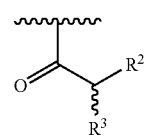

formula (II)

wherein $R^2$ is hydrogen or amino; and $R^3$ is amino, guanidino, $C_1$-$C_6$ alkyl substituted with an amino or guanidino moiety, or a natural or unnatural amino acid side chain;

or b) $R^1$, when taken together with the nitrogen to which it is attached, forms a guanidine moiety;

wherein at least 25% of $R^1$ substituents are H, at least 1% of $R^1$ substituents are acetyl, and at least 2% of $R^1$ substituents are a group of formula (II) or are taken together with the nitrogen to which they are attached to form a guanidine moiety.

In some embodiments, between 25-95% of $R^1$ substituents are hydrogen.

In some embodiments, between 55-90% of $R^1$ substituents are hydrogen.

In some embodiments, between 1-50% of $R^1$ substituents are acetyl.

In some embodiments, between 4-20% of $R^1$ substituents are acetyl.

In some embodiments, between 2-50% of $R^1$ substituents are a group of formula (II).

In some embodiments, between 4-30% of $R^1$ substituents are a group of formula (II).

In some embodiments, 55-90% of $R^1$ substituents are hydrogen, 4-20% of $R^1$ substituents are acetyl, 4-30% of $R^1$ substituents are a group of formula (II).

In some embodiments, $R^2$ is amino and $R^3$ is an arginine side chain.

In some embodiments, $R^1$ is selected from one of the following:

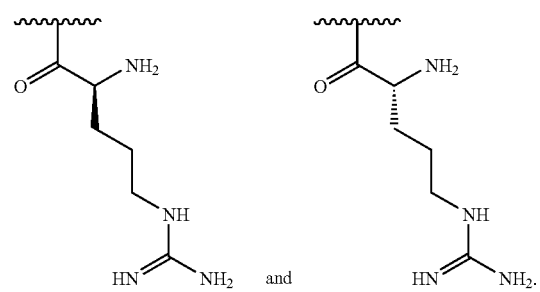 [SMILES: *C(=O)[C@@H](N)CCCNC(=N)N ; "and" ; *C(=O)[C@H](N)CCCNC(=N)N]

In some embodiments, $R^2$ is amino and $R^3$ is a lysine side chain.

In some embodiments, $R^1$ is selected from one of the following:

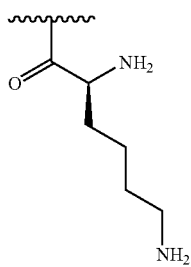 and 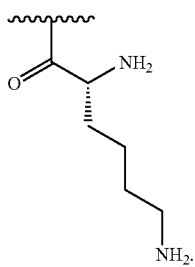

In some embodiments, $R^2$ is amino and $R^3$ is a histidine side chain.

In some embodiments, $R^1$ is selected from one of the following:

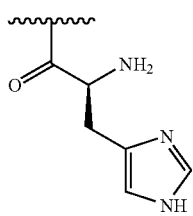 and 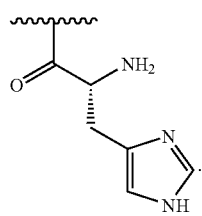

In some embodiments, at least 1% of $R^1$ substituents are selected from one of the following:

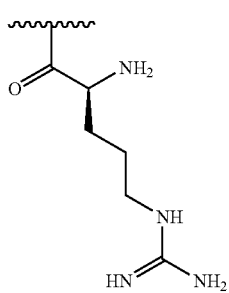 and 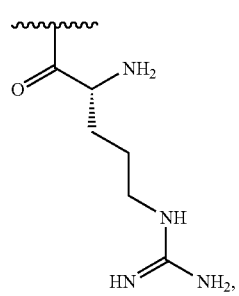

AND at least 1% of $R^1$ substituents are selected from the following:

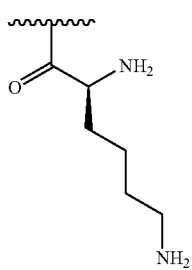 and 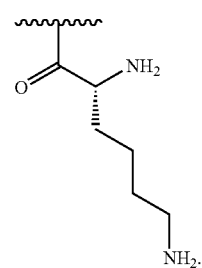

In some embodiments, $R^2$ is amino and $R^3$ is a substituted $C_1$-$C_6$ alkyl.

In some embodiments, $R^3$ is $C_1$-$C_6$ alkyl substituted with an amino group.

In some embodiments, $R^3$ is $C_1$ alkyl substituted with an amino group.

In some embodiments, $R^3$ is $C_2$ alkyl substituted with an amino group.

In some embodiments, $R^3$ is $C_3$ alkyl substituted with an amino group.

In some embodiments, $R^1$ is selected from one of the following:

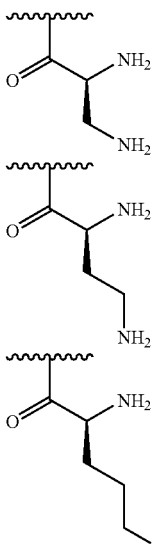 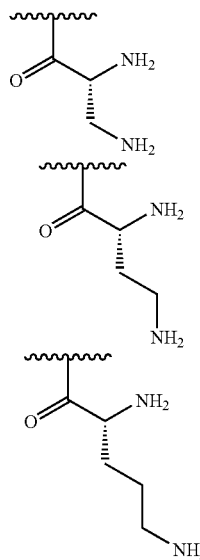

In some embodiments, $R^3$ is $C_1$-$C_6$ alkyl substituted with a guanidino group.

In some embodiments, $R^3$ is $C_1$ alkyl substituted with a guanidino group.

In some embodiments, $R^3$ is $C_2$ alkyl substituted with a guanidino group.

In some embodiments, $R^1$ is selected from one of the following:

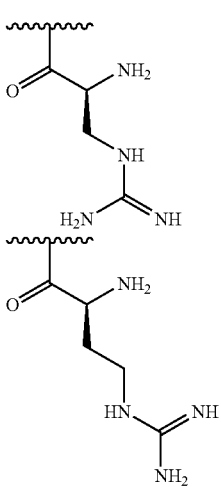 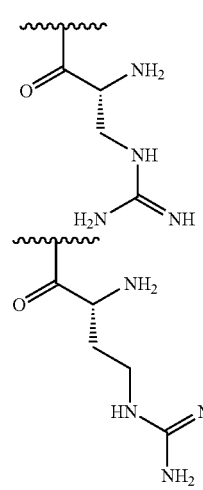

In some embodiments, $R^2$ is amino that is substituted with a nitrogen protecting group prior to substitution on chitosan and removed subsequent to substitution on chitosan.

In some embodiments, the nitrogen protecting group is tert-butyloxycarbonyl (Boc).

In some embodiments, in the synthetic process a nitrogen protecting group is used, which can provide an intermediate polymer having a nitrogen protecting group such as Boc.

In some embodiments, $R^2$ is amino.

In some embodiments, $R^2$ is hydrogen and $R^3$ is amino.

In some embodiments, $R^2$ is hydrogen and $R^3$ is guanidino.

In some embodiments, $R^2$ is hydrogen and $R^3$ is a substituted $C_1$-$C_6$ alkyl.

In some embodiments, $R^3$ is $C_1$-$C_6$ alkyl substituted with an amino group.

In some embodiments, $R^3$ is $C_1$ alkyl substituted with an amino group.

In some embodiments, $R^3$ is $C_2$ alkyl substituted with an amino group.

In some embodiments, $R^3$ is $C_3$ alkyl substituted with an amino group.

In some embodiments, $R^3$ is $C_4$ alkyl substituted with an amino group.

In some embodiments, $R^3$ is $C_5$ alkyl substituted with an amino group.

In some embodiments, $R^1$ is selected from one of the following:

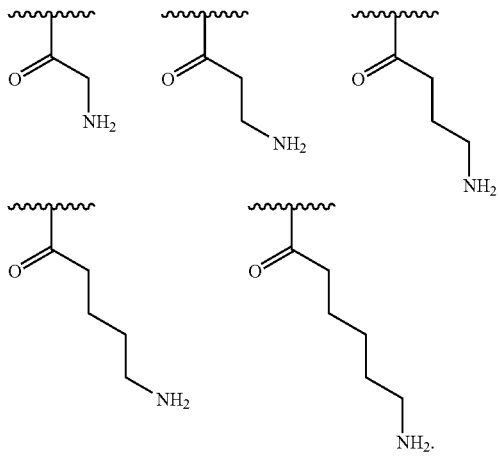

In some embodiments, $R^3$ is $C_1$-$C_6$ alkyl substituted with a guanidino group.

In some embodiments, $R^3$ is $C_1$ alkyl substituted with a guanidino group.

In some embodiments, $R^3$ is $C_2$ alkyl substituted with a guanidino group.

In some embodiments, $R^3$ is $C_3$ alkyl substituted with a guanidino group.

In some embodiments, $R^3$ is $C_4$ alkyl substituted with a guanidino group.

In some embodiments, $R^3$ is $C_5$ alkyl substituted with a guanidino group.

In some embodiments, $R^1$ is selected from one of the following:

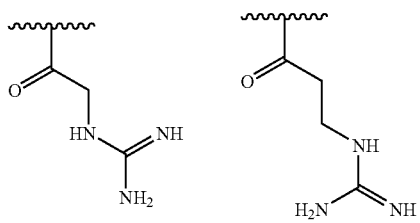

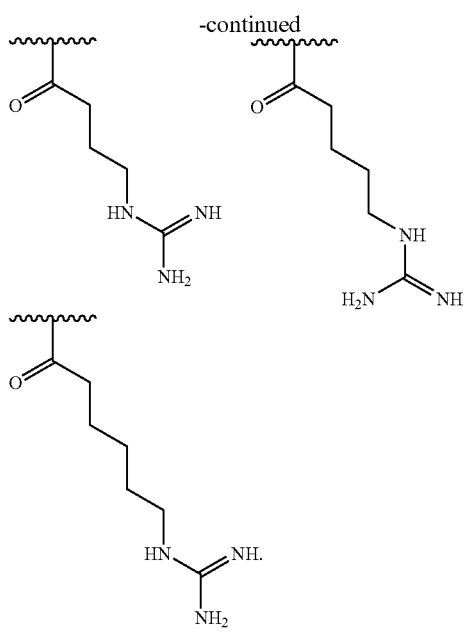

In some embodiments, at least 25% of $R^1$ substituents are H, at least 1% of $R^1$ substituents are acetyl, and at least 2% of $R^1$ substituents independently selected from any of the formulae specifically shown above.

In some embodiments, the chitosan of formula (I) may be further derivatized on the free hydroxyl moieties.

In some embodiments, the molecular weight of the derivatized chitosan is between 5,000 and 1,000,000 Da.

In some embodiments, the molecular weight of the derivatized chitosan is between 5,000 and 350,000 Da.

In some embodiments, the molecular weight of the derivatized chitosan is between 10,000 and 150,000 Da.

In some embodiments, the molecular weight of the derivatized chitosan is between 15,000 and 100,000 Da.

In some embodiments, the molecular weight of the derivatized chitosan is between 20,000 and 30,000 Da.

In some embodiments, the chitosan is functionalized at between 5% and 50%.

In a preferred embodiment, the chitosan is functionalized at between 20% and 30%.

In some embodiments, the degree of deacetylation (% DDA) of the derivatized chitosan is between 75% and 95%.

In some embodiments, the degree of deacetylation (% DDA) of the derivatized chitosan is between 80% and 90%.

In some embodiments, the polydispersity index (PDI) of the derivatized chitosan is between 1.0 and 2.5.

In some embodiments, the polydispersity index (PDI) of the derivatized chitosan is between 1.5 and 2.0.

In some embodiments, the functionalized chitosan is substantially free of other impurities, e.g., salt, e.g., NaCl.

In some embodiments, the MDR bacterium is selected from a bacterium listed in Table 1A.

In some embodiments, the MDR bacterium comprises resistance to an anti-bacterial agent selected from the group consisting of aminoglycosides; beta-lactam antibiotics; macrolides; antibiotic polypeptides; antibiotic lipopeptides; antibiotic glycopeptides; monobactams; quinolones; sulfonamides; and tetracyclines, and a bacterium is selected from Table 1A.

In some embodiments, the chitosan derivative is chitosan derivatized with arginine, and the MDR bacterium is selected from the group consisting of methicillin resistant *Staphylococcus aureus* (MRSA) and human clinical isolates of MRSA; *Acinetobacter baumannii*; *Kelbsiella pneumoniae*;

Mupirocin resistant MRSA (MMRSA); Vancoymicn resistant *Enterococcus faecium* (VRE); *Salmonella enterica* serovar typhimurium and *Pseudomonas aeruginosa*.

In some embodiments, the chitosan derivative is administered with an antibacterial agent is selected from the group consisting of aminoglycosides; beta-lactam antibiotics; macrolides; antibiotic polypeptides; antibiotic lipopeptides; antibiotic glycopeptides; monobactams; quinolones; sulfonamides; and tetracyclines.

In another aspect, the invention features a method of reducing the transmission of MDR by an MDR bacterium relative to an MDR bacterium untreated with the derivatized chitosan and/or the acquisition of MDR by a non-MDR bacterium relative to a non-MDR bacterium untreated with the derivatized chitosan in a subject, or, reducing MDR bacterial load in a subject, e.g., inhibiting the growth of MDR bacteria or killing the MDR bacteria, or protecting a subject from exposure to an MDR bacterium, comprising: optionally, identifying the subject as at risk of infection with an MDR bacterium, infected with an MDR bacterium, in need of reduced MDR bacterial load, in need of protection from exposure to an MDR bacterium, or as one that would otherwise benefit from rendering an MDR bacterium less able to transmit MDR to another bacterium; and administering an effective amount of a derivatized chitosan; thereby reducing the transmission of MDR by an MDR bacterium relative to an MDR bacterium untreated with the derivatized chitosan and/or the acquisition of MDR by a non-MDR bacterium relative to a non-MDR bacterium untreated with the derivatized chitosan in a subject, or, reducing MDR bacterial load in a subject, e.g., inhibiting the growth of MDR bacteria or killing the MDR bacteria, or protecting a subject from exposure to an MDR bacterium.

In some embodiments, the derivatized chitosan reduces the transmission of MDR by an MDR bacterium relative to an MDR bacterium untreated with the derivatized chitosan in a subject by at least about 25% (e.g., at least about 50%, at least about 60%, at least about 70%, at least about 80%, at least about 90%, at least about 95%, or at least about 99%). In some embodiments, the derivatized chitosan reduces the acquisition of MDR by a non-MDR bacterium relative to a non-MDR bacterium untreated with the derivatized chitosan in a subject by at least about 25% (e.g., at least about 50%, at least about 60%, at least about 70%, at least about 80%, at least about 90%, at least about 95%, or at least about 99%)

In some embodiments, the inhibition is in vivo, in the body of a subject.

In some embodiments, the inhibition is in vitro or ex vivo, or otherwise not in the body of a subject.

In some embodiments, the MDR bacterium is identified as an MDR strain before, at the time of, or after said administration.

In some embodiments, the derivatized chitosan is soluble at physiological pH, e.g., from about 6.8 to about 7.4.

In some embodiments, the derivatized chitosan is soluble in aqueous solution from about pH 3 to about pH 9.

In some embodiments, the derivatized chitosan comprises a chitosan of the following formula (I):

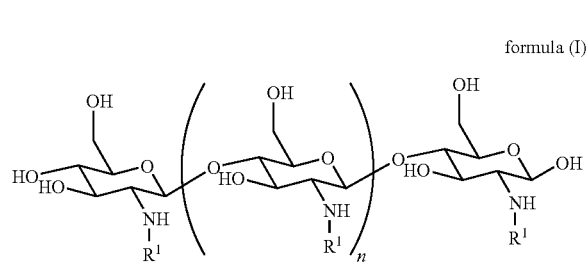

formula (I)

wherein:

n is an integer between 20 and 6000; and each $R^1$ is independently selected for each occurrence from hydrogen, acetyl, and either:

a) a group of formula (II):

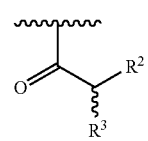

formula (II)

wherein $R^2$ is hydrogen or amino; and $R^3$ is amino, guanidino, $C_1$-$C_6$ alkyl substituted with an amino or guanidino moiety, or a natural or unnatural amino acid side chain;

or b) $R^1$, when taken together with the nitrogen to which it is attached, forms a guanidine moiety;

wherein at least 25% of $R^1$ substituents are H, at least 1% of $R^1$ substituents are acetyl, and at least 2% of $R^1$ substituents are a group of formula (II) or are taken together with the nitrogen to which they are attached to form a guanidine moiety.

In some embodiments, between 25-95% of $R^1$ substituents are hydrogen.

In some embodiments, between 55-90% of $R^1$ substituents are hydrogen.

In some embodiments, between 1-50% of $R^1$ substituents are acetyl.

In some embodiments, between 4-20% of $R^1$ substituents are acetyl.

In some embodiments, between 2-50% of $R^1$ substituents are a group of formula (II).

In some embodiments, between 4-30% of $R^1$ substituents are a group of formula (II).

In some embodiments, 55-90% of $R^1$ substituents are hydrogen, 4-20% of $R^1$ substituents are acetyl, 4-30% of $R^1$ substituents are a group of formula (II).

In some embodiments, $R^2$ is amino and $R^3$ is an arginine side chain.

In some embodiments, $R^1$ is selected from one of the following:

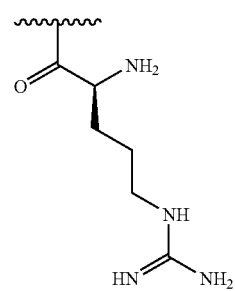 and 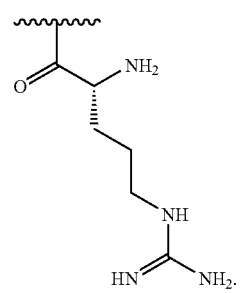

In some embodiments, $R^2$ is amino and $R^3$ is a lysine side chain.

In some embodiments, R¹ is selected from one of the following:

[Two chemical structures showing lysine-like side chains with NH₂ groups, labeled "and"]

In some embodiments, R² is amino and R³ is a histidine side chain.

In some embodiments, R¹ is selected from one of the following:

[Two chemical structures showing histidine-like side chains, labeled "and"]

In some embodiments, at least 1% of R¹ substituents are selected from one of the following:

[Two chemical structures showing arginine-like side chains with guanidino groups, labeled "and"]

AND at least 1% of R¹ substituents are selected from the following:

[Two chemical structures showing lysine-like side chains with NH₂ groups, labeled "and"]

In some embodiments, R² is amino and R³ is a substituted $C_1$-$C_6$ alkyl.

In some embodiments, R³ is $C_1$-$C_6$ alkyl substituted with an amino group.

In some embodiments, R³ is $C_1$ alkyl substituted with an amino group.

In some embodiments, R³ is $C_2$ alkyl substituted with an amino group.

In some embodiments, R³ is $C_3$ alkyl substituted with an amino group.

In some embodiments, R¹ is selected from one of the following:

[Multiple chemical structures showing various amino acid side chains with NH₂ groups]

In some embodiments, R³ is $C_1$-$C_6$ alkyl substituted with a guanidino group.

In some embodiments, R³ is $C_1$ alkyl substituted with a guanidino group.

In some embodiments, R³ is $C_2$ alkyl substituted with a guanidino group.

In some embodiments, R¹ is selected from one of the following:

[Multiple chemical structures showing various amino acid side chains with guanidino groups]

In some embodiments, R² is amino that is substituted with a nitrogen protecting group prior to substitution on chitosan and removed subsequent to substitution on chitosan.

In some embodiments, the nitrogen protecting group is tert-butyloxycarbonyl (Boc).

In some embodiments, in the synthetic process a nitrogen protecting group is used, which can provide an intermediate polymer having a nitrogen protecting group such as Boc.

In some embodiments, $R^2$ is amino.

In some embodiments, $R^2$ is hydrogen and $R^3$ is amino

In some embodiments, $R^2$ is hydrogen and $R^3$ is guanidino.

In some embodiments, $R^2$ is hydrogen and $R^3$ is a substituted $C_1$-$C_6$ alkyl.

In some embodiments, $R^3$ is $C_1$-$C_6$ alkyl substituted with an amino group.

In some embodiments, $R^3$ is $C_1$ alkyl substituted with an amino group.

In some embodiments, $R^3$ is $C_2$ alkyl substituted with an amino group.

In some embodiments, $R^3$ is $C_3$ alkyl substituted with an amino group.

In some embodiments, $R^3$ is $C_4$ alkyl substituted with an amino group.

In some embodiments, $R^3$ is $C_5$ alkyl substituted with an amino group.

In some embodiments, $R^1$ is selected from one of the following:

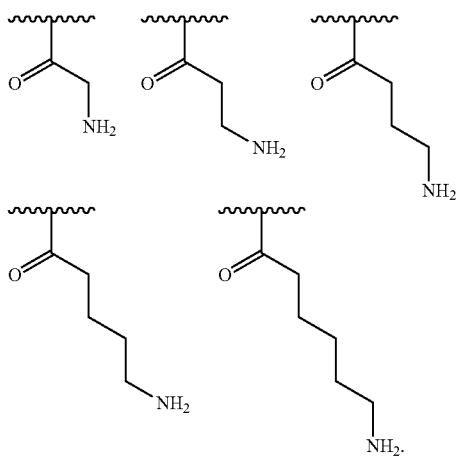

In some embodiments, $R^3$ is $C_1$-$C_6$ alkyl substituted with a guanidino group.

In some embodiments, $R^3$ is $C_1$ alkyl substituted with a guanidino group.

In some embodiments, $R^3$ is $C_2$ alkyl substituted with a guanidino group.

In some embodiments, $R^3$ is $C_3$ alkyl substituted with a guanidino group.

In some embodiments, $R^3$ is $C_4$ alkyl substituted with a guanidino group.

In some embodiments, $R^3$ is $C_5$ alkyl substituted with a guanidino group.

In some embodiments, $R^1$ is selected from one of the following:

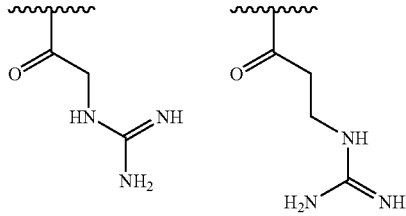

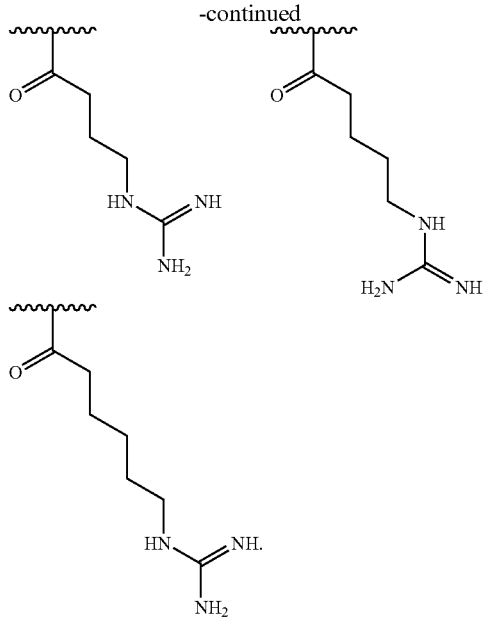

In some embodiments, at least 25% of $R^1$ substituents are H, at least 1% of $R^1$ substituents are acetyl, and at least 2% of $R^1$ substituents independently selected from any of the formulae specifically shown above.

In some embodiments, the chitosan of formula (I) may be further derivatized on the free hydroxyl moieties.

In some embodiments, the molecular weight of the derivatized chitosan is between 5,000 and 1,000,000 Da.

In some embodiments, the molecular weight of the derivatized chitosan is between 5,000 and 350,000 Da.

In some embodiments, the molecular weight of the derivatized chitosan is between 10,000 and 150,000 Da.

In some embodiments, the molecular weight of the derivatized chitosan is between 15,000 and 100,000 Da.

In some embodiments, the molecular weight of the derivatized chitosan is between 20,000 and 30,000 Da.

In some embodiments, the chitosan is functionalized at between 5% and 50%.

In a preferred embodiment, the chitosan is functionalized at between 20% and 30%.

In some embodiments, the degree of deacetylation (% DDA) of the derivatized chitosan is between 75% and 95%.

In some embodiments, the degree of deacetylation (% DDA) of the derivatized chitosan is between 80% and 90%.

In some embodiments, the polydispersity index (PDI) of the derivatized chitosan is between 1.0 and 2.5.

In some embodiments, the polydispersity index (PDI) of the derivatized chitosan is between 1.5 and 2.0.

In some embodiments, the functionalized chitosan is substantially free of other impurities, e.g., salt, e.g., NaCl.

In some embodiments, the MDR bacterium is selected from a bacterium listed in Table 1A.

In some embodiments, the MDR comprises resistance to an anti-bacterial agent selected from the group consisting of aminoglycosides; beta-lactam antibiotics; macrolides; antibiotic polypeptides; antibiotic lipopeptides; antibiotic glycopeptides; monobactams; quinolones; sulfonamides; and tetracyclines, and a bacterium is selected from Table 1A.

In some embodiments, the chitosan derivative is chitosan derivatized with arginine, and the MDR bacterium is selected from the group consisting of methicillin resistant *Staphylococcus aureus* (MRSA) and human clinical isolates of MRSA; *Acinetobacter baumannii*; *Kelbsiella pneumoniae*;

Mupirocin resistant MRSA (MMRSA); Vancoymicn resistant *Enterococcus faecium* (VRE); *Salmonella enterica* serovar typhimurium and *Pseudomonas aeruginosa*.

In some embodiments, the chitosan derivative is administered with an antibacterial agent is selected from the group consisting of aminoglycosides; beta-lactam antibiotics; macrolides; antibiotic polypeptides; antibiotic lipopeptides; antibiotic glycopeptides; monobactams; quinolones; sulfonamides; and tetracyclines.

In some embodiments, the subject was determined to be at risk for exposure to or infection with an MDR bacterium.

In some embodiments, a person having primary or secondary contact with the subject has been diagnosed as being infected with an MDR bacterium.

In some embodiments, the derivatized chitosan is administered orally. In some embodiments, the derivatized chitosan is administered locally, e.g., topically, e.g., to a wound.

In some embodiments, the derivatized chitosan is administered as a rinse or lavage.

In some embodiments, the subject is suffering from a disorder characterized by the presence of one or more of the pathogens described herein.

In yet another aspect, the invention features a pharmaceutical composition comprising a chitosan derivative in amount effective to inhibit transfer of MDR by an MDR bacterium.

In one aspect, the invention features a kit comprising at least two unit doses of a pharmaceutical composition comprising a chitosan derivative in amount effective to inhibit transfer of MDR by an MDR bacterium.

In some embodiments, one of said unit doses has a higher amount of chitosan derivative than the other.

In one aspect, the invention features a medical device, e.g., a wound dressing or implantable device, which comprises comprising a chitosan derivative in an amount effective to inhibit transfer of MDR by an MDR bacterium.

In another aspect, the invention features a method of protecting a surface from acquiring an MDR bacterium, or inhibiting the transfer of MDR by an MDR bacterium, or acquisition of MDR by a non-MDR bacterium, on a surface, the method comprising:

optionally, identifying a surface as contaminated with or at risk for contamination with an MDR bacterium; optionally, selecting a composition described herein on the basis of it being able to inhibit transfer of MDR by an MDR bacterium, or acquisition of MDR by a non-MDR bacterium; and contacting the surface with said composition; thereby protecting a surface from acquiring an MDR bacterium, or inhibiting the transfer of MDR by an MDR bacterium, or acquisition of MDR by a non-MDR bacterium, on a surface.

In some embodiments, said surface is the surface of a medical device, a surface present in a building, e.g., a counter, sink, control, e.g., light switch or water control.

In some embodiments, said surface is the surface of a medical device, which is placed in contact with a subject.

In another aspect, the invention features a method of reducing biofilm viscosity by positive chitosan derivatives, and in particular, the reduction of biofilms and supernatant of MDR *Pseudomonas aeruginosa* by chitosan-arginine. In particular such biofilms are in the CF lung.

In one aspect, the invention features a method of inhibiting the growth of a bacterium and/or killing a bacterium. The method includes contacting the bacterium with a derivatized chitosan and an anti-bacterial agent in an effective combined amount, thereby inhibiting the growth of the bacterium and/or killing a bacterium.

In some embodiments, the anti-bacterial agent and derivatized chitosan are present at a concentration, or administered at a dose, which results in a synergistic effect, e.g., the inhibition is greater, e.g., at least 2, 4, 10, 20, 50, or 100 times greater, than the sum of the inhibition seen with either used alone. In some embodiments, the anti-bacterial agent is present at a concentration, or administered at a dose, which is less than the lowest concentration, or dose, that would give maximum inhibition in the absence of the derivatized chitosan. In some embodiments, the anti-bacterial agent is present at a concentration, or administered at a dose, which is less than the lowest concentration, or dose, generally used to treat infections of the bacterium. In some embodiments, the anti-bacterial agent is present at a concentration, or administered at a dose, which is less than 90, 80, 70, 60, 50, 40, 30, 20, 10, 5, 1, 0.1, 0.01% of the lowest concentration, or dose, that would give maximum inhibition in the absence of the derivatized chitosan. In some embodiments, the anti-bacterial agent is present at a concentration, or administered at a dose, which is less than 90, 80, 70, 60, 50, 40, 30, 20, 10, 5, 1, 0.1, 0.01% of the lowest concentration, or dose, generally used to treat infections of the bacterium. In some embodiments, the anti-bacterial agent and derivatized chitosan are present at a concentration, or administered at a dose, which are lower than the MIC of at least one of the anti-bacterial agent or derivatized chitosan when administered in the absence the other. In some embodiments, the anti-bacterial agent and derivatized chitosan are present at a concentration, or administered at a dose, which have an FIC less than about 0.5, 0.4, 0.3, 0.2, 0.1, 0.05, or 0.01. In some embodiments, the anti-bacterial agent is present at a concentration, or administered at a dose, which would not result in substantial inhibition of bacterial growth in the absence of the derivatized chitosan. In some embodiments, the anti-bacterial agent is present at a concentration, or administered at a dose, which would not result in clinical or therapeutic levels of inhibition of bacterial growth in the absence of the derivatized chitosan.

In some embodiments, the bacterium is a resistant bacterium (e.g., resistant to the administration of the chitosan derivative in the absence of the antibiotic and/or resistant to the administration of the antibiotic in the absence of the chitosan derivative). In some embodiments, the anti-bacterial agent and derivatized chitosan are present at a concentration, or administered at a dose, which results in sensitizing the resistant bacterium. In some embodiments, the bacterium is resistant to the anti-bacterial agent in the absence the derivatized chitosan. In some embodiments, the bacterium is resistant to the derivatized chitosan in the absence the anti-bacterial agent. In some embodiments, the anti-bacterial agent is present at a concentration, or administered at a dose, which would not result in substantial inhibition of bacterial growth and/or killing the bacterium in the absence of the derivatized chitosan. In some embodiments, the derivatized chitosan is present at a concentration, or administered at a dose, which would not result in substantial inhibition of bacterial growth and/or killing the bacterium in the absence of the anti-bacterial agent. In some embodiments, the anti-bacterial agent is present at a concentration, or administered at a dose, which would not result in clinical or therapeutic levels of inhibition of bacterial growth and/or killing the bacterium in the absence of the derivatized chitosan. In some embodiments, the derivatized chitosan is present at a concentration, or administered at a dose, which would not result in clinical or therapeutic levels of inhibition of bacterial growth and/or killing the bacterium in the absence of the anti-bacterial agent. In some embodiments, the anti-bacterial agent and derivatized chitosan are present at a concentration, or administered at a dose, which are lower than the MIC of at least one of the anti-bacterial agent or derivatized chitosan when administered in the absence of the other. In some embodiments, the anti-bacterial agent and derivatized chitosan are present at a concentration, or administered at a dose, which result in a bactericidal activity at least about 2, 2.5, 3, 3.5, 4, 4.5, or 5 logs more effective than the most effective activity in the absence of the chitosan derivative or anti-bacterial agent, e.g., the activity of the chitosan derivative in the absence of the anti-bacterial agent or the anti-bacterial agent in the absence of the chitosan derivative.

In some embodiments, the resistant bacterium is identified as a resistant bacterium before, at the time of, or after said contact.

In some embodiments, the derivatized chitosan is soluble at physiological pH, e.g., from about 6.8 to about 7.4.

In some embodiments, the derivatized chitosan is soluble in aqueous solution from about pH 3 to about pH 9.

In some embodiments, the derivatized chitosan comprises a chitosan of the following formula (I):

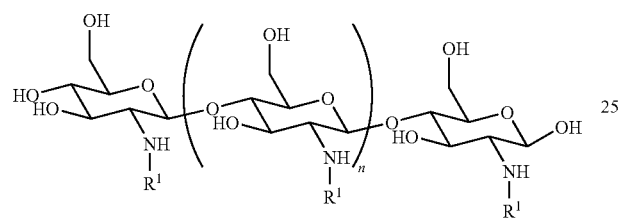

formula (I)

wherein:
n is an integer between 20 and 6000; and
each $R^1$ is independently selected for each occurrence from hydrogen, acetyl, and either:
a) a group of formula (II):

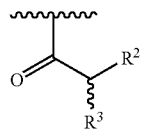

formula (II)

wherein $R^2$ is hydrogen or amino; and
$R^3$ is amino, guanidino, $C_1$-$C_6$ alkyl substituted with an amino or guanidino moiety, or a natural or unnatural amino acid side chain;
or b) $R^1$, when taken together with the nitrogen to which it is attached, forms a guanidine moiety;
wherein at least 25% of $R^1$ substituents are H, at least 1% of $R^1$ substituents are acetyl, and at least 2% of $R^1$ substituents are a group of formula (II) or are taken together with the nitrogen to which they are attached to form a guanidine moiety.

In some embodiments, between 25-95% of $R^1$ substituents are hydrogen.

In some embodiments, between 55-90% of $R^1$ substituents are hydrogen.

In some embodiments, between 1-50% of $R^1$ substituents are acetyl.

In some embodiments, between 4-20% of $R^1$ substituents are acetyl.

In some embodiments, between 2-50% of $R^1$ substituents are a group of formula (II).

In some embodiments, between 4-30% of $R^1$ substituents are a group of formula (II).

In some embodiments, 55-90% of $R^1$ substituents are hydrogen, 4-20% of $R^1$ substituents are acetyl, 4-30% of $R^1$ substituents are a group of formula (II).

In some embodiments, $R^2$ is amino and $R^3$ is an arginine side chain.

In some embodiments, $R^1$ is selected from one of the following:

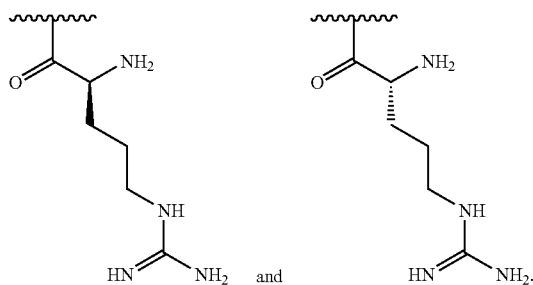

In some embodiments, $R^2$ is amino and $R^3$ is a lysine side chain.

In some embodiments, $R^1$ is selected from one of the following:

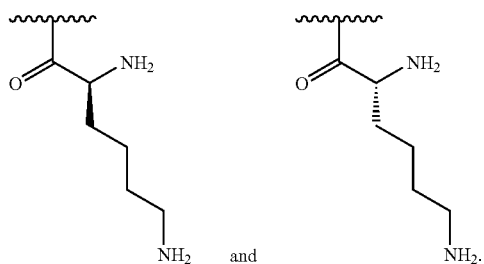

In some embodiments, $R^2$ is amino and $R^3$ is a histidine side chain.

In some embodiments, $R^1$ is selected from one of the following:

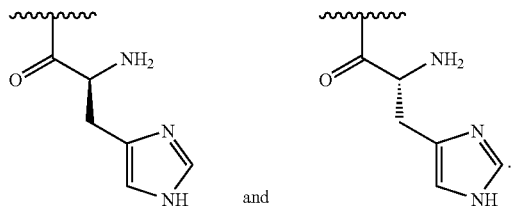 [SMILES: *C(=O)[C@@H](N)Cc1c[nH]cn1 ; *C(=O)[C@H](N)Cc1c[nH]cn1]

In some embodiments, at least 1% of $R^1$ substituents are selected from one of the following:

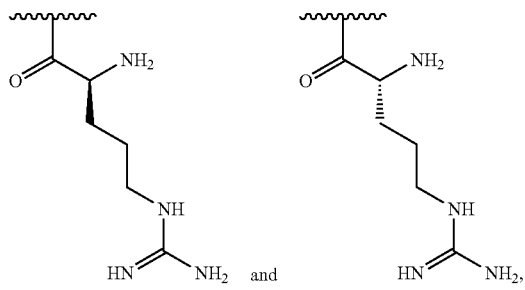

AND at least 1% of $R^1$ substituents are selected from the following:

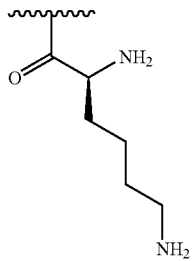 and 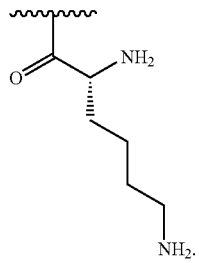

In some embodiments, $R^2$ is amino and $R^3$ is a substituted $C_1$-$C_6$ alkyl.

In some embodiments, $R^3$ is $C_1$-$C_6$ alkyl substituted with an amino group.

In some embodiments, $R^3$ is $C_1$ alkyl substituted with an amino group.

In some embodiments, $R^3$ is $C_2$ alkyl substituted with an amino group.

In some embodiments, $R^3$ is $C_3$ alkyl substituted with an amino group.

In some embodiments, $R^1$ is selected from one of the following:

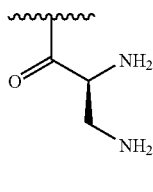 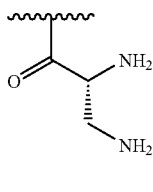 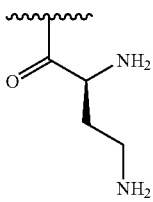

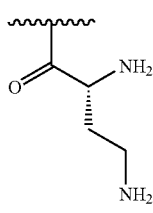 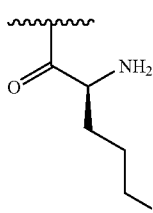

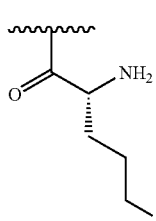

In some embodiments, $R^3$ is $C_1$-$C_6$ alkyl substituted with a guanidino group.

In some embodiments, $R^3$ is $C_1$ alkyl substituted with a guanidino group.

In some embodiments, $R^3$ is $C_2$ alkyl substituted with a guanidino group.

In some embodiments, $R^1$ is selected from one of the following:

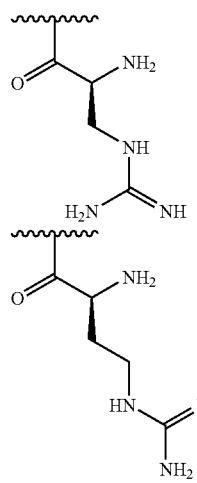 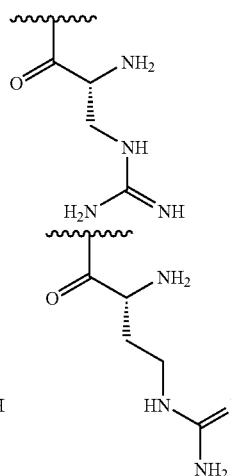

In some embodiments, $R^2$ is amino that is substituted with a nitrogen protecting group prior to substitution on chitosan and removed subsequent to substitution on chitosan.

In some embodiments, the nitrogen protecting group is tert-butyloxycarbonyl (Boc).

In some embodiments, in the synthetic process a nitrogen protecting group is used, which can provide an intermediate polymer having a nitrogen protecting group such as Boc.

In some embodiments, $R^2$ is amino.
In some embodiments, $R^2$ is hydrogen and $R^3$ is amino.
In some embodiments, $R^2$ is hydrogen and $R^3$ is guanidino.
In some embodiments, $R^2$ is hydrogen and $R^3$ is a substituted $C_1$-$C_6$ alkyl.

In some embodiments, $R^3$ is $C_1$-$C_6$ alkyl substituted with an amino group.

In some embodiments, $R^3$ is $C_1$ alkyl substituted with an amino group.

In some embodiments, $R^3$ is $C_2$ alkyl substituted with an amino group.

In some embodiments, $R^3$ is $C_3$ alkyl substituted with an amino group.

In some embodiments, $R^3$ is $C_4$ alkyl substituted with an amino group.

In some embodiments, $R^3$ is $C_5$ alkyl substituted with an amino group.

In some embodiments, $R^1$ is selected from one of the following:

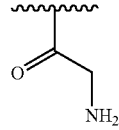 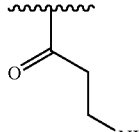 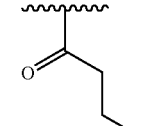

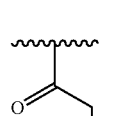 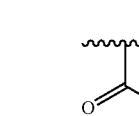 

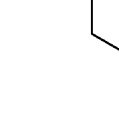 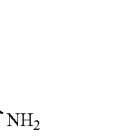 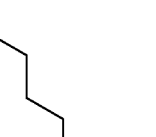

In some embodiments, $R^3$ is $C_1$-$C_6$ alkyl substituted with a guanidino group.

In some embodiments, $R^3$ is $C_1$ alkyl substituted with a guanidino group.

In some embodiments, $R^3$ is $C_2$ alkyl substituted with a guanidino group.

In some embodiments, $R^3$ is $C_3$ alkyl substituted with a guanidino group.

In some embodiments, $R^3$ is $C_4$ alkyl substituted with a guanidino group.

In some embodiments, $R^3$ is $C_5$ alkyl substituted with a guanidino group.

In some embodiments, $R^1$ is selected from one of the following:

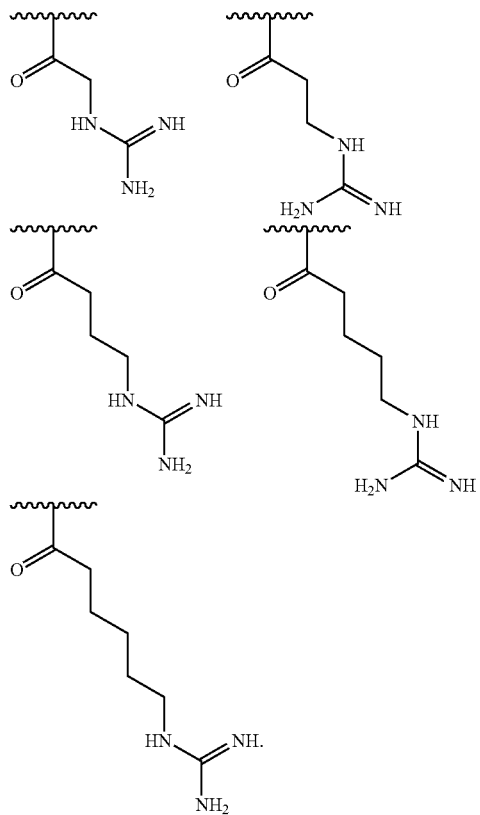

In some embodiments, at least 25% of $R^1$ substituents are H, at least 1% of $R^1$ substituents are acetyl, and at least 2% of $R^1$ substituents independently selected from any of the formulae specifically shown above.

In some embodiments, the chitosan of formula (I) may be further derivatized on the free hydroxyl moieties.

In some embodiments, the molecular weight of the derivatized chitosan is between 5,000 and 1,000,000 Da.

In some embodiments, the molecular weight of the derivatized chitosan is between 5,000 and 350,000 Da.

In some embodiments, the molecular weight of the derivatized chitosan is between 10,000 and 150,000 Da.

In some embodiments, the molecular weight of the derivatized chitosan is between 15,000 and 100,000 Da.

In some embodiments, the molecular weight of the derivatized chitosan is between 20,000 and 30,000 Da.

In some embodiments, the chitosan is functionalized between 5% and 50%.

In a preferred embodiment, the chitosan is functionalized at between 20% and 30%.

In some embodiments, the degree of deacetylation (% DDA) of the derivatized chitosan is between 75% and 95%.

In some embodiments, the degree of deacetylation (% DDA) of the derivatized chitosan is between 80% and 90%.

In some embodiments, the polydispersity index (PDI) of the derivatized chitosan is between 1.0 and 2.5.

In some embodiments, the polydispersity index (PDI) of the derivatized chitosan is between 1.5 and 2.0.

In some embodiments, the functionalized chitosan is substantially free of other impurities, e.g., salt, e.g., NaCl.

In some embodiments, the derivatized chitosan and anti-bacterial agent are administered simultaneously, in either sequence, discreetly or overlapping.

In some embodiments, the derivatized chitosan is chitosan derivatized with a basic amino acid. In some embodiments, the derivatized chitosan is chitosan derivatized with arginine. In some embodiments, the molecular weight of the derivatized chitosan is from about 25 to about 100 kDa.

In some embodiments, the anti-bacterial agent is selected from the group consisting of Gram-negative, Gram-positive, and broad spectrum antibiotic. In some embodiments, the anti-bacterial agent is selected from the group consisting of aminoglycosides; beta-lactam antibiotics; macrolides; antibiotic polypeptides; antibiotic lipopeptides; antibiotic glycopeptides; monobactams; quinolones; sulfonamides; and tetracyclines.

In some embodiments, the chitosan derivative is chitosan derivatized with arginine, the anti-bacterial agent is selected from aminoglycosides; beta-lactam antibiotics; macrolides; antibiotic polypeptides; antibiotic lipopeptides; antibiotic glycopeptides; monobactams; quinolones; sulfonamides; and tetracyclines, and the bacterium is selected from Gram-positive and Gram-negative bacterium.

In some embodiments, the chitosan derivative is chitosan derivatized with arginine, the anti-bacterial agent is selected from Ciprofloxacin, Rifampicin, Neomycin, silver and Gentamicin and the bacterium is *Pseudomonas aeruginosa*.

In some embodiments, the bacterium is selected from a bacteria listed in Table 1B.

In some embodiments, the bacterium is selected from a bacteria listed in Table 1C.

In one aspect, the invention features a method of treating a subject for a bacterial infection or disorder, reducing bacterial load in a subject, e.g., inhibiting the growth of bacteria or killing the bacteria, or treating a symptom of bacterial infection. The method includes administering a derivatized chitosan (e.g., soluble at physiological pH, e.g., from about 6.8 to about 7.4) and an anti-bacterial agent in an effective combined amount, thereby treating a subject for a bacterial infection, reducing bacterial load, e.g., inhibiting the growth of bacteria or killing the bacteria, or treating a symptom of bacterial infection. The method includes optionally, identifying the subject as at risk of infection with a bacterium, infected with a bacterium, in need of reduced bacterial load, in need of protection from exposure to a bacterium, having a symptom of bacterial infection, or as one that would otherwise benefit from rendering a bacterium sensitive to an anti-bacterial agent.

In some embodiments, the anti-bacterial agent and derivatized chitosan are present at a concentration, or administered at a dose, which results in a synergistic effect, e.g., the inhibition is greater, e.g., at least 2, 4, 10, 20, 50, or 100 times greater, than the sum of the inhibition seen with either used alone. In some embodiments, the anti-bacterial agent is present at a concentration, or administered at a dose, which is less than the lowest concentration, or dose, that would give maximum inhibition in the absence of the derivatized chitosan. In some embodiments, the anti-bacterial agent is present at a concentration, or administered at a dose, which is less than the lowest concentration, or dose, generally used to treat infections of the bacterium. In some embodiments, the anti-bacterial agent is present at a concentration, or administered at a dose, which is less than 90, 80, 70, 60, 50, 40, 30, 20, 10, 5, 1, 0.1, 0.01% of the lowest concentration, or dose, that would give maximum inhibition in the absence of the derivatized chitosan. In some embodiments, the anti-bacterial agent is present at a concentration, or administered at a dose, which is less than 90, 80, 70, 60, 50, 40, 30, 20, 10, 5, 1, 0.1, 0.01% of the lowest concentration, or dose, generally used to treat infections of the bacterium. In some embodiments, the anti-bacterial agent and derivatized chitosan are present at a concentration, or administered at a dose, which are lower than the MIC of at least one of the anti-bacterial agent or derivatized chitosan when administered in the abasence the other. In some embodiments, the anti-bacterial agent and derivatized chitosan are present at a concentration, or administered at a dose, which have an FIC less than about 0.5, 0.4, 0.3, 0.2, 0.1, 0.05, or 0.01. In some embodiments, the anti-bacterial agent is present at a concentration, or administered at a dose, which would not result in substantial inhibition of bacterial growth in the absence of the derivatized chitosan. In some embodiments, the anti-bacterial agent is present at a concentration, or administered at a dose, which would not result in clinical or therapeutic levels of inhibition of bacterial growth in the absence of the derivatized chitosan.

In some embodiments, the bacterium is a resistant bacterium (e.g., resistant to the administration of the chitosan derivative in the absence of the antibiotic and/or resistant to the administration of the antibiotic in the absence of the chitosan derivative). In some embodiments, the anti-bacterial agent and derivatized chitosan are present at a concentration, or administered at a dose, which results in sensitizing a resistant bacterium. In some embodiments, the bacterium is resistant to the anti-bacterial agent in the absence the derivatized chitosan. In some embodiments, the bacterium is resistant to the derivatized chitosan in the absence the anti-bacterial agent. In some embodiments, the anti-bacterial agent is present at a concentration, or administered at a dose, which would not result in substantial inhibition of bacterial growth in the absence of the derivatized chitosan. In some embodiments, the derivatized chitosan is present at a concentration, or administered at a dose, which would not result in substantial inhibition of bacterial growth or killing the bacterium in the absence of the anti-bacterial agent. In some embodiments, the anti-bacterial agent is present at a concentration, or administered at a dose, which would not result in clinical or therapeutic levels of inhibition of bacterial growth or killing the bacterium in the absence of the derivatized chitosan. In some embodiments, the anti-bacterial agent and derivatized chitosan are present at a concentration, or administered at a dose, which are lower than the MIC of at least one of the anti-bacterial agent or derivatized chitosan when administered in the absence of the other. In some embodiments, the anti-bacterial agent and derivatized chitosan are present at a concentration, or administered at a dose, which result in a bactericidal activity at least about 2, 2.5, 3, 3.5, 4, 4.5, or 5 logs more effective than the most effective activity in the absence of the chitosan derivative or anti-bacterial agent, e.g., the activity of the chitosan derivative in the absence of the anti-bacterial agent or the anti-bacterial agent in the absence of the chitosan derivative.

In some embodiments, the resistant bacterium is identified as a resistant bacterium before, at the time of, or after said contact.

In some embodiments, the derivatized chitosan is soluble in aqueous solution from about pH 6.8 to about pH 7.4.

In some embodiments, the derivatized chitosan is soluble in aqueous solution from about pH 3 to about pH 9.

In some embodiments, the derivatized chitosan comprises a chitosan of the following formula (I):

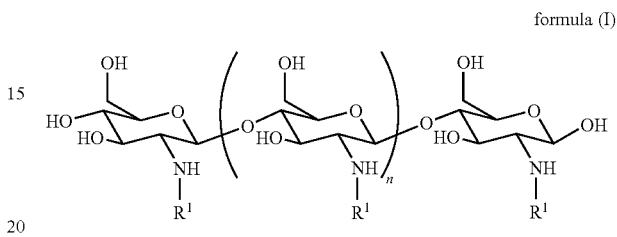

formula (I)

wherein:

n is an integer between 20 and 6000; and each $R^1$ is independently selected for each occurrence from hydrogen, acetyl, and either:

a) a group of formula (II):

formula (II)

wherein $R^2$ is hydrogen or amino; and $R^3$ is amino, guanidino, $C_1$-$C_6$ alkyl substituted with an amino or guanidino moiety, or a natural or unnatural amino acid side chain;

or b) $R^1$, when taken together with the nitrogen to which it is attached, forms a guanidine moiety;

wherein at least 25% of $R^1$ substituents are H, at least 1% of $R^1$ substituents are acetyl, and at least 2% of $R^1$ substituents are a group of formula (II) or are taken together with the nitrogen to which they are attached to form a guanidine moiety.

In some embodiments, between 25-95% of $R^1$ substituents are hydrogen.

In some embodiments, between 55-90% of $R^1$ substituents are hydrogen.

In some embodiments, between 1-50% of $R^1$ substituents are acetyl.

In some embodiments, between 4-20% of $R^1$ substituents are acetyl.

In some embodiments, between 2-50% of $R^1$ substituents are a group of formula (II).

In some embodiments, between 4-30% of $R^1$ substituents are a group of formula (II).

In some embodiments, 55-90% of $R^1$ substituents are hydrogen, 4-20% of $R^1$ substituents are acetyl, 4-30% of $R^1$ substituents are a group of formula (II).

In some embodiments, $R^2$ is amino and $R^3$ is an arginine side chain.

In some embodiments, $R^1$ is selected from one of the following:

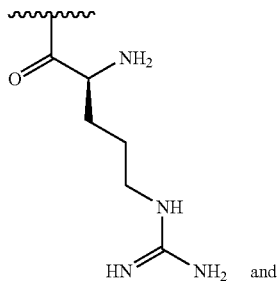 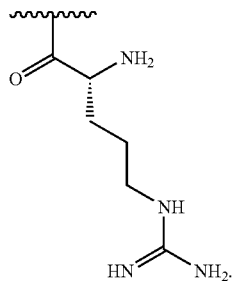

In some embodiments, $R^2$ is amino and $R^3$ is a lysine side chain.

In some embodiments, $R^1$ is selected from one of the following:

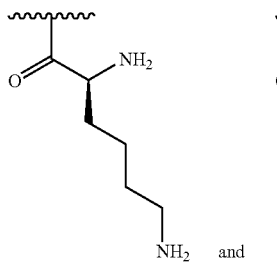 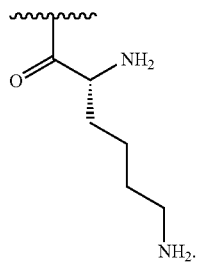

In some embodiments, $R^2$ is amino and $R^3$ is a histidine side chain.

In some embodiments, $R^1$ is selected from one of the following:

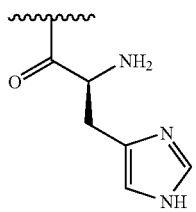 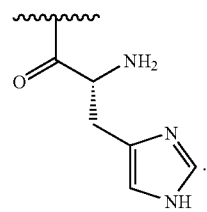

In some embodiments, at least 1% of $R^1$ substituents are selected from one of the following:

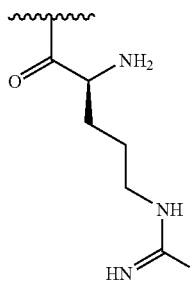 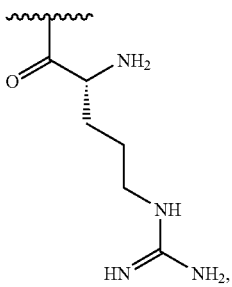

AND at least 1% of $R^1$ substituents are selected from the following:

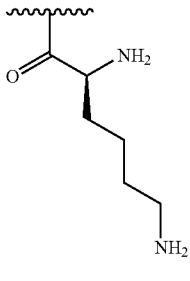 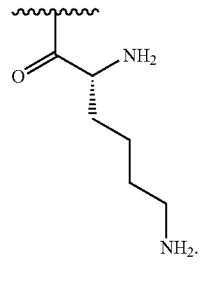

In some embodiments, $R^2$ is amino and $R^3$ is a substituted $C_1$-$C_6$ alkyl.

In some embodiments, $R^3$ is $C_1$-$C_6$ alkyl substituted with an amino group.

In some embodiments, $R^3$ is $C_1$ alkyl substituted with an amino group.

In some embodiments, $R^3$ is $C_2$ alkyl substituted with an amino group.

In some embodiments, $R^3$ is $C_3$ alkyl substituted with an amino group.

In some embodiments, $R^1$ is selected from one of the following:

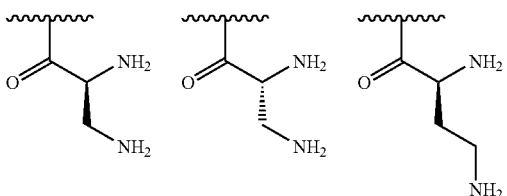

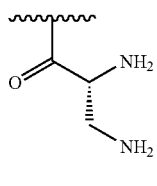 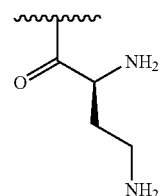

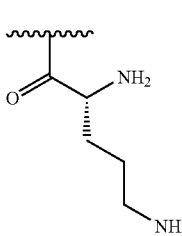

In some embodiments, $R^3$ is $C_1$-$C_6$ alkyl substituted with a guanidino group.

In some embodiments, $R^3$ is $C_1$ alkyl substituted with a guanidino group.

In some embodiments, $R^3$ is $C_2$ alkyl substituted with a guanidino group.

In some embodiments, $R^1$ is selected from one of the following:

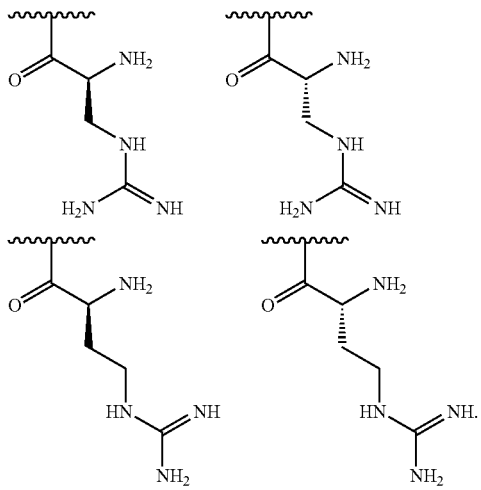

In some embodiments, $R^2$ is amino that is substituted with a nitrogen protecting group prior to substitution on chitosan and removed subsequent to substitution on chitosan.

In some embodiments, the nitrogen protecting group is tert-butyloxycarbonyl (Boc).

In some embodiments, in the synthetic process a nitrogen protecting group is used, which can provide an intermediate polymer having a nitrogen protecting group such as Boc.

In some embodiments, $R^2$ is amino.

In some embodiments, $R^2$ is hydrogen and $R^3$ is amino.

In some embodiments, $R^2$ is hydrogen and $R^3$ is guanidino.

In some embodiments, $R^2$ is hydrogen and $R^3$ is a substituted $C_1$-$C_6$ alkyl.

In some embodiments, $R^3$ is $C_1$-$C_6$ alkyl substituted with an amino group.

In some embodiments, $R^3$ is $C_1$ alkyl substituted with an amino group.

In some embodiments, $R^3$ is $C_2$ alkyl substituted with an amino group.

In some embodiments, $R^3$ is $C_3$ alkyl substituted with an amino group.

In some embodiments, $R^3$ is $C_4$ alkyl substituted with an amino group.

In some embodiments, $R^3$ is $C_5$ alkyl substituted with an amino group.

In some embodiments, $R^1$ is selected from one of the following:

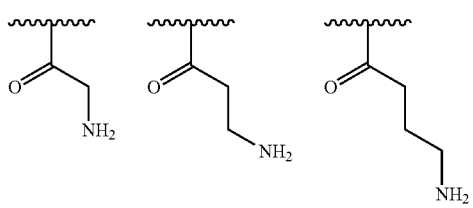

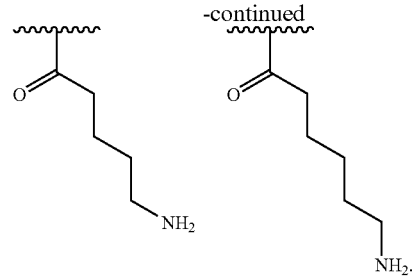

In some embodiments, $R^3$ is $C_1$-$C_6$ alkyl substituted with a guanidino group.

In some embodiments, $R^3$ is $C_1$ alkyl substituted with a guanidino group.

In some embodiments, $R^3$ is $C_2$ alkyl substituted with a guanidino group.

In some embodiments, $R^3$ is $C_3$ alkyl substituted with a guanidino group.

In some embodiments, $R^3$ is $C_4$ alkyl substituted with a guanidino group.

In some embodiments, $R^3$ is $C_5$ alkyl substituted with a guanidino group.

In some embodiments, $R^1$ is selected from one of the following:

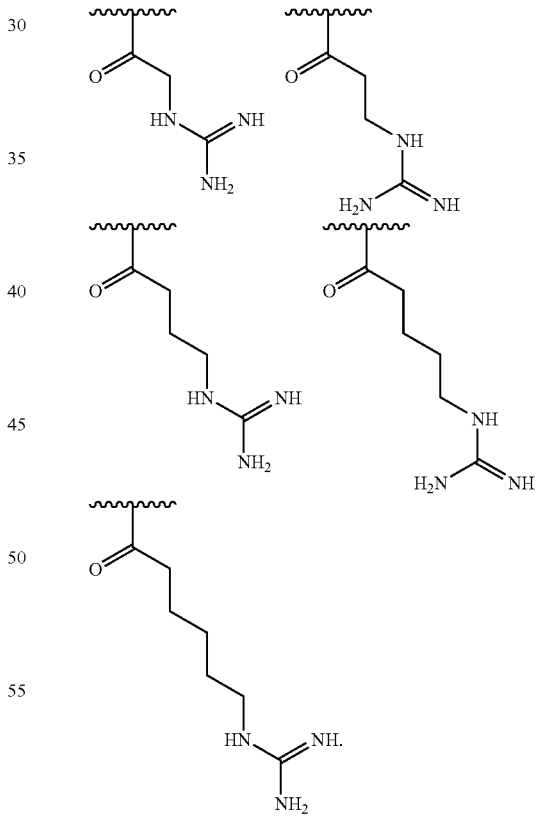

In some embodiments, at least 25% of $R^1$ substituents are H, at least 1% of $R^1$ substituents are acetyl, and at least 2% of $R^1$ substituents independently selected from any of the formulae specifically shown above.

In some embodiments, the chitosan of formula (I) may be further derivatized on the free hydroxyl moieties.

In some embodiments, the molecular weight of the derivatized chitosan is between 5,000 and 1,000,000 Da.

In some embodiments, the molecular weight of the derivatized chitosan is between 5,000 and 350,000 Da.

In some embodiments, the molecular weight of the derivatized chitosan is between 10,000 and 150,000 Da.

In some embodiments, the molecular weight of the derivatized chitosan is between 15,000 and 100,000 Da.

In some embodiments, the molecular weight of the derivatized chitosan is between 20,000 and 30,000 Da.

In some embodiments, the chitosan is functionalized at between 5% and 50%.

In a preferred embodiment, the chitosan is functionalized at between 20% and 30%.

In some embodiments, the degree of deacetylation (% DDA) of the derivatized chitosan is between 75% and 95%.

In some embodiments, the degree of deacetylation (% DDA) of the derivatized chitosan is between 80% and 90%.

In some embodiments, the polydispersity index (PDI) of the derivatized chitosan is between 1.0 and 2.5.

In some embodiments, the polydispersity index (PDI) of the derivatized chitosan is between 1.5 and 2.0.

In some embodiments, the functionalized chitosan is substantially free of other impurities, e.g., salt, e.g., NaCl.

In some embodiments, the derivatized chitosan and anti-bacterial agent are administered simultaneously, in either sequence, discreetly or overlapping. In some embodiments, the anti-bacterial agent is administered systemically and the derivatized chitosan is administered orally, topically, bucally or enterally. In some embodiments, the derivatized chitosan is chitosan derivatized with a basic amino acid. In some embodiments, the derivatized chitosan is chitosan derivatized with arginine. In some embodiments, the molecular weight of the derivatized chitosan is from about 25 to about 100 kDa.

In some embodiments, the anti-bacterial agent is selected from the group consisting of Gram-negative, Gram-positive, and broad spectrum antibiotic. In some embodiments, the anti-bacterial agent is selected from the group consisting of aminoglycosides; beta-lactam antibiotics; macrolides; antibiotic polypeptides; antibiotic lipopeptides; antibiotic glycopeptides; monobactams; quinolones; sulfonamides; and tetracyclines.

In some embodiments, the chitosan derivative is chitosan derivatized with arginine, the anti-bacterial agent is selected from aminoglycosides; beta-lactam antibiotics; macrolides; antibiotic polypeptides; antibiotic lipopeptides; antibiotic glycopeptides; monobactams; quinolones; sulfonamides; and tetracyclines, and the bacterium is selected from Gram-positive and Gram-negative bacterium.

In some embodiments, the chitosan derivative is chitosan derivatized with arginine, the anti-bacterial agent is selected from Ciprofloxacin, Rifampicin, Neomycin, silver or Gentamicin and the bacterium is *Pseudomonas aeruginosa*.

In some embodiments, the bacterium is selected from a bacteria listed in Table 1B.

In some embodiments, the bacterium is selected from a bacteria listed in Table 1C.

In some embodiments, the subject is suffering from a *Pseudomonas aeruginosa* infection.

In some embodiments, the infection or disorder has previously been treated with an anti-bacterial agent without a chitosan derivative and, e.g., said treatment was unsatisfactory.

In some embodiments, the derivatized chitosan and an anti-bacterial agent are administered orally. In some embodiments, the derivatized chitosan and an anti-bacterial agent are administered locally, e.g., topically, e.g., to a wound. In some embodiments the derivatized chitosan and an anti-bacterial agent are delivered intra-nasally, or inhaled or to the gastrointestinal tract.

In one aspect, the invention features pharmaceutical composition including a chitosan derivative and an anti-bacterial agent. In some embodiments, at least one of the chitosan derivative or anti-bacterial agent is present in an amount less than would be required to be effective if administered to a subject in the absence of the other (e.g., the chitosan derivative is present in an amount less than required to be effective in the absence of the anti-bacterial agent and/or the antibacterial agent is present in an amount less than required to be effective in the absence of the chitosan derivative). In some embodiments, the pharmaceutical composition includes a chitosan derivative and an anti-bacterial agent in a combined amount effective to inhibit the growth and/or kill a resistant bacterium. In some embodiments, the bacterium is resistant to the anti-bacterial agent in the absence the derivatized chitosan. In some embodiments, the bacterium is resistant to the derivatized chitosan in the absence the anti-bacterial agent.

In one aspect, the invention features a kit including at least two unit doses of a pharmaceutical composition comprising a chitosan derivative and an anti-bacterial agent. In some embodiments, at least one of the chitosan derivative or anti-bacterial agent is present in an amount less than would be required to be effective if administered to a subject in the absence of the other (e.g., the chitosan derivative is present in an amount less than required to be effective in the absence of the anti-bacterial agent and/or the antibacterial agent is present in an amount less than required to be effective in the absence of the chitosan derivative). In some embodiments, the kit includes at least two unit doses of a pharmaceutical composition comprising a chitosan derivative and an anti-bacterial agent in a combined amount effective to inhibit the growth and/or kill a resistant bacterium. In some embodiments, the bacterium is resistant to the anti-bacterial agent in the absence the derivatized chitosan. In some embodiments, the bacterium is resistant to the derivatized chitosan in the absence the anti-bacterial agent. In some embodiments, one of said unit doses has a higher amount of anti-bacterial agent than the other.

In one aspect, the invention features medical device, e.g., a wound dressing or implantable device, which includes a chitosan derivative and an anti-bacterial agent. In some embodiments, at least one of the chitosan derivative or anti-bacterial agent is present in an amount less than would be required to be effective if administered to a subject in the absence of the other (e.g., the chitosan derivative is present in an amount less than required to be effective in the absence of the anti-bacterial agent and/or the antibacterial agent is present in an amount less than required to be effective in the absence of the chitosan derivative). In some embodiments, the medical device includes a chitosan derivative and anti-bacterial agent in a combined amount effective to inhibit the growth and.or kill a resistant bacterium. In some embodiments, the bacterium is resistant to the anti-bacterial agent in the absence the derivatized chitosan. In some embodiments, the bacterium is resistant to the derivatized chitosan in the absence the anti-bacterial agent.

The combinations of derivatized chitosan and an anti-microbial agent such as an antibiotic as described herein can also have an effect that sensitizes resistant bacteria to the antibacterials to which they were resistant when used to treat a subject having a resistant bacterial infection.

In one aspect, the invention features a method of protecting a surface from growth of a resistant bacterium comprising: optionally, identifying a surface contaminated with or at risk for contamination with a resistant bacterium; optionally, selecting a composition described herein on the basis of it being able to inhibit the growth of a resistant bacterium; contacting the surface with said composition; thereby protecting a surface from growth of a resistant bacterium comprising.

In some embodiments, said surface is the surface of a medical device, a surface present in a building, e.g., a counter, sink, control. e.g., light switch or water control.

DETAILED DESCRIPTION

Overview

Figure 1:
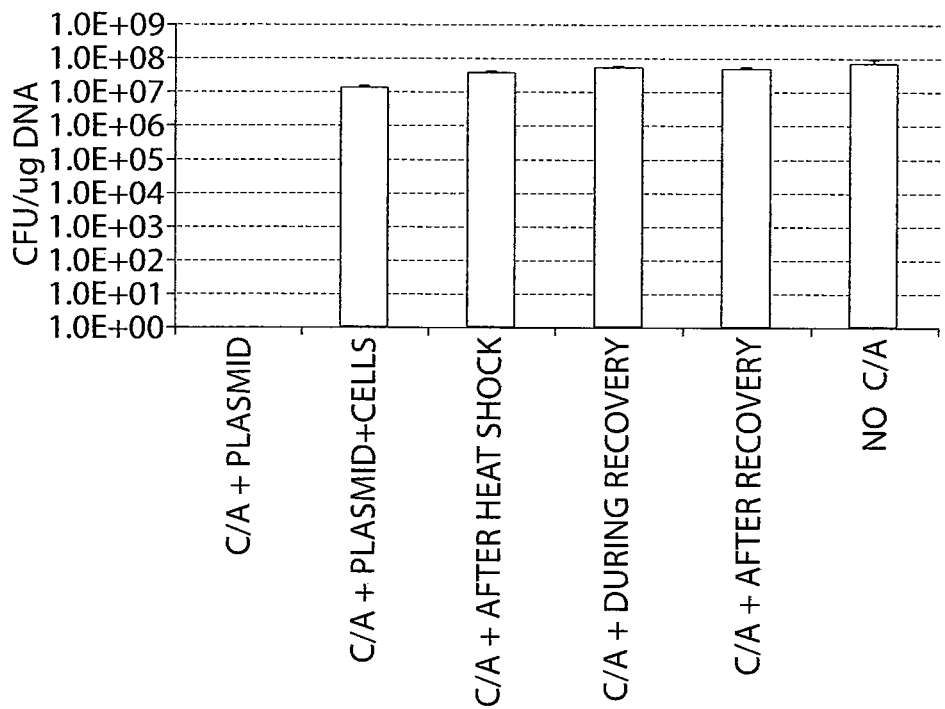
FIG. 1 depicts inhibition of plasmid transformation by chitosan-arginine.

Soluble chitosans and derivatized chitosans are described herein. Described herein are also compositions and methods for treating bacterial infections and/or inhibiting the growth of bacteria using a soluble chitosan or derivatized chitosan. A subject having a bacterial infection can be treated by the compositions and methods described herein. Exemplary compositions and methods generally include use of a soluble chitosan or derivatized chitosan.

For example, described herein are compositions containing a soluble chitosan or derivatized chitosan and methods of using a soluble chitosan or derivatized chitosan to treat and/or inhibit acquisition of a multiple drug resistance (MDR) bacteria.

Described herein are also compositions containing a combination of a soluble chitosan or derivatized chitosan described herein and an anti-bacterial agent, and methods of using a soluble chitosan or derivatized chitosan in combination with an anti-bacterial agent for treating bacterial infections and/or inhibiting the growth of bacteria. In some embodiments, the combination of a soluble chitosan and derivatized chitosan and an anti-bacterial agent results in a synergistic effect, e.g., a reduced minimum inhibitory concentration (MIC) of either the soluble chitosan or chitosan derivative, or the anti-bacterial agent, or both. In some embodiments, the combination of a soluble chitosan and derivatized chitosan and an anti-bacterial agent results in sensitizing a bacterium (e.g., overcoming the breakpoint) that was previously resistant to the anti-bacterial agent.

Soluble Chitosans and Chitosan Derivatives

Compounds and compositions containing a soluble chitosan or a chitosan derivative for treating or preventing bacterial infections and/or inhibiting the growth of bacteria are described herein. The soluble chitosan or a chitosan derivative can be administered to a subject in a method described herein, for example in a composition or dosage form described herein.

Chitosan is an insoluble polymer derived from chitin, which is a polymer of N-acetylglucosamine. It is the main component of the exoskeletons of crustaceans (e.g. shrimp, crab, lobster). Chitosan is formed from chitin by deacetylation, and thus is a random copolymer of glucosamine and N-acetylglucosamine monomers. Chitosan is therefore not a single polymeric molecule, but a class of molecules having various molecular weights and various degrees of deacetylation. The degree of deacetylation determines the relative content of free amino groups to total monomers in the chitosan polymer. The percent deacetylation in commercial chitosans is typically between 50-100%. Chitosans with any degree of deacetylation (DDA) greater than 50% are used in the present invention. Methods that can be used for determination of the degree of deacetylation of chitosan include, e.g., ninhydrin test, linear potentiometric titration, near-infrared spectroscopy, nuclear magnetic resonance spectroscopy, hydrogen bromide titrimetry, infrared spectroscopy, and first derivative UV-spectrophotometry. Preferably, the degree of deacetylation of a soluble chitosan or a derivatized chitosan described herein is determined by quantitative infrared spectroscopy.

The chitosan derivatives described herein are generated by functionalizing the resulting free amino groups with positively charged or neutral moieties, as described herein. Chitosans with functionalization between 2% and 50% of the available amines are used in the present invention. Percent functionalization is determined as the % of derivatized amines relative to the total number of available amino moieties prior to reaction on the chitosan polymer. Preferably, the percent functionalization of a derivatized chitosan described herein is determined by H-NMR or quantitative elemental analysis.

The degrees of deacetylation and functionalization impart a specific charge density to the functionalized chitosan derivative. The resulting charge density affects solubility, and the strength of interaction with bacterial cell walls and membranes. The molecular weight is also an important factor in the tenacity of bacterial wall interaction and thus bactericidal activity. Thus, in accordance with the present invention, the degree of deacetylation, the functionalization and the molecular weight must be optimized for optimal efficacy.

The derivatized chitosans described herein have a number of properties which are advantageous including solubility at physiologic pH and antimicrobial activity when in solution or dry at any pH less than about 9. Exemplary chitosan derivatives are described in Baker et al; Ser. No. 11/657,382 filed on Jan. 24, 2007, which is incorporated herein by reference.

A soluble chitosan as described herein, refers to a water soluble chitosan that is not derivatized on the hydroxyl or amine moieties. Generally a water soluble chitosan has a molecular weight of less than or equal to about 10 kDa and a degree of deacetylation equal or greater than 80%. Water soluble is defined as being fully dissolvable in water at pH 7.

The chitosan derivatives described herein have a range of polydispersity index (PDI) between about 1.0 to about 2.5. As used herein, the polydispersity index (PDI), is a measure of the distribution of molecular weights in a given polymer sample. The PDI calculated is the weight averaged molecular weight divided by the number averaged molecular weight. This calculation indicates the distribution of individual molecular weights in a batch of polymers. The PDI has a value always greater than 1, but as the polymer chains approach uniform chain length, the PDI approaches unity (1). The PDI of a polymer derived from a natural source depends on the natural source (e.g. chitin or chitosan from crab vs. shrimp vs. fungi) and can be affected by a variety of reaction, production, processing, handling, storage and purifying conditions. Methods to determine the polydispersity include, e.g., gel permeation chromatography (also known as size exclusion chromatography); light scattering measurements; and direct calculation from MALDI or from electrospray mass spectrometry. Preferably, the PDI of a soluble chitosan or a derivatized chitosan described herein is determined by HPLC and multi angle light scattering methods.

The chitosan derivatives described herein have a range of molecular weights that are soluble at neutral and physiological pH, and include for the purposes of this invention molecular weights ranging from 5-1,000 kDa. Embodiments described herein feature moderate molecular weights of derivatized chitosans (25 kDa, e.g., from about 15 to about 300 kDa) which can have clumping, diffusible and biofilm disruption properties.

The functionalized chitosan derivatives described herein include the following:

(A) Chitosan-arginine compounds;
(B) Chitosan-natural amino acid derivative compounds;
(C) Chitosan-unnatural amino acid compounds;
(D) Chitosan-acid amine compounds;
(E) Chitosan-guanidine compounds; and
(F) Neutral chitosan derivative compounds.

(A) Chitosan-Arginine Compounds

In some embodiments, the present invention is directed to chitosan-arginine compounds, where the arginine is bound through a peptide(amide) bond via its carbonyl to the primary amine on the glucosamines of chitosan:

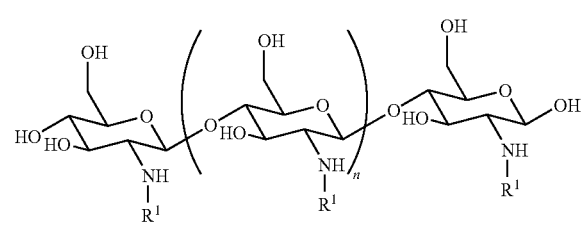

wherein each $R^1$ is independently selected from hydrogen, acetyl, and a group of the following formula:

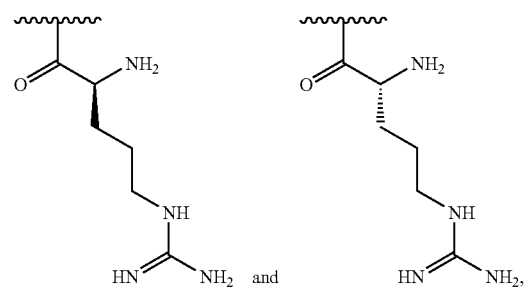

or a racemic mixture thereof,
wherein at least 25% of $R^1$ substituents are H, at least 1% are acetyl, and at least 2% are a group of the formula shown above.

(B) Chitosan-Natural Amino Acid Derivative Compounds

In some embodiments, the present invention is directed to chitosan-natural amino acid derivative compounds, wherein the natural amino acid may be histidine or lysine. The amino is bound through a peptide(amide) bond via its carbonyl to the primary amine on the glucosamines of chitosan:

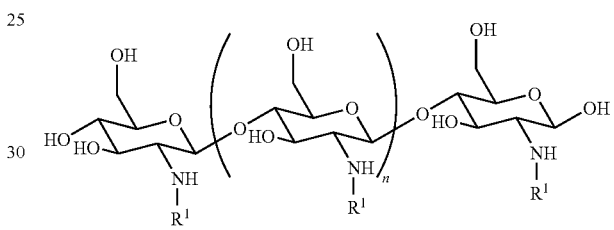

wherein each $R^1$ is independently selected from hydrogen, acetyl, and a group of the following formula:

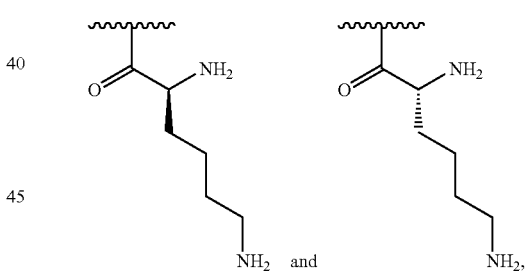

or a racemic mixture thereof, wherein at least 25% of $R^1$ substituents are H, at least 1% are acetyl, and at least 2% are a group of the formula shown above; OR a group of the following formula:

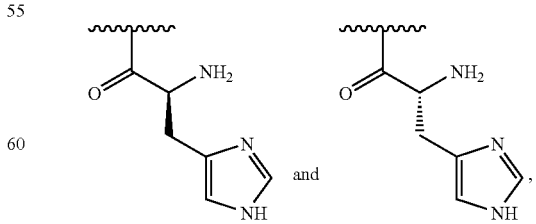

or a racemic mixture thereof, wherein at least 25% of $R^1$ substituents are H, at least 1% are acetyl, and at least 2% are a group of the formula shown above.

(C) Chitosan-Unnatural Amino Acid Compounds

In some embodiments, the present invention is directed to chitosan-unnatural amino acid compounds, where the unnatural amino acid is bound through a peptide(amide) bond via its carbonyl to the primary amine on the glucosamines of chitosan:

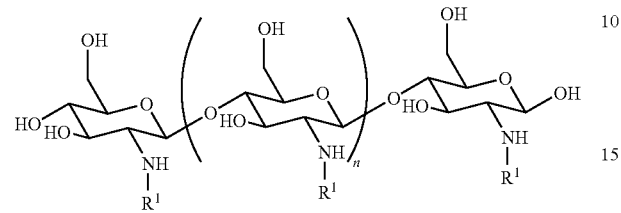

wherein each $R^1$ is independently selected from hydrogen, acetyl, and a group of the following formula:

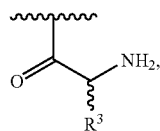

wherein $R^3$ is an unnatural amino acid side chain, and wherein at least 25% of $R^1$ substituents are H, at least 1% are acetyl, and at least 2% are a group of the formula shown above.

Unnatural amino acids are those with side chains not normally found in biological systems, such as ornithine (2,5-diaminopentanoic acid). Any unnatural amino acid may be used in accordance with the invention. In some embodiments, the unnatural amino acids coupled to chitosan have the following formulae:

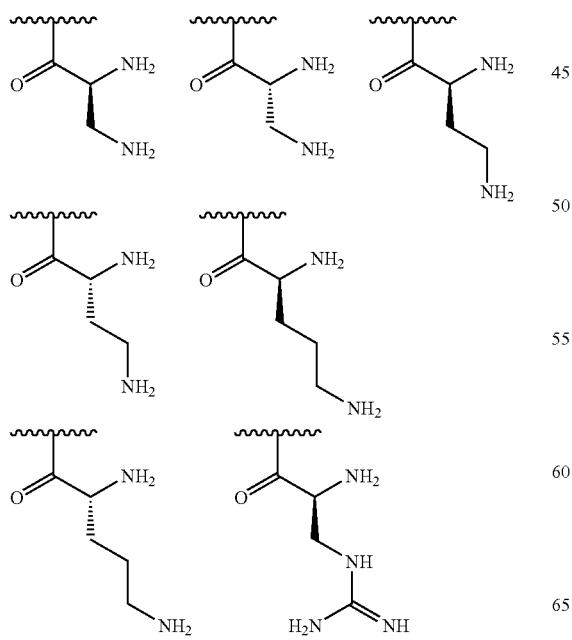

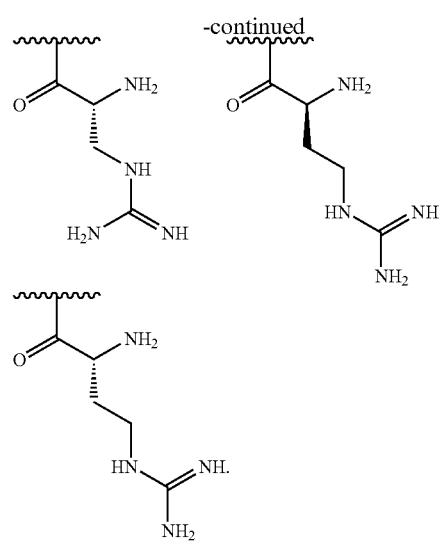

(D) Chitosan-Acid Amine and Guanidine Compounds

In some embodiments, the present invention is directed to chitosan-acid amine compounds, or their guanidylated counterparts. The acid amine is bound through a peptide(amide) bond via its carbonyl to the primary amine on the glucosamines of chitosan:

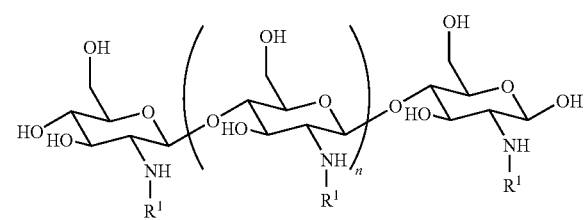

wherein each $R^1$ is independently selected from hydrogen, acetyl, and a group of the following formula:

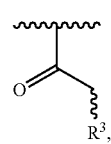

wherein $R^3$ is selected from amino, guanidino, and $C_1$-$C_6$ alkyl substituted with an amino or a guanidino group, wherein at least 25% of $R^1$ substituents are H, at least 1% are acetyl, and at least 2% are a group of the formula shown above In some embodiments, $R^1$ is selected from one of the following:

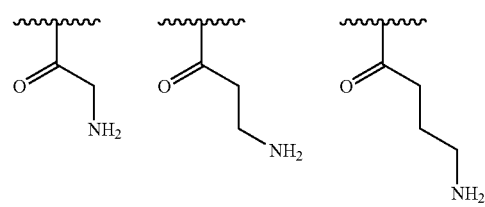

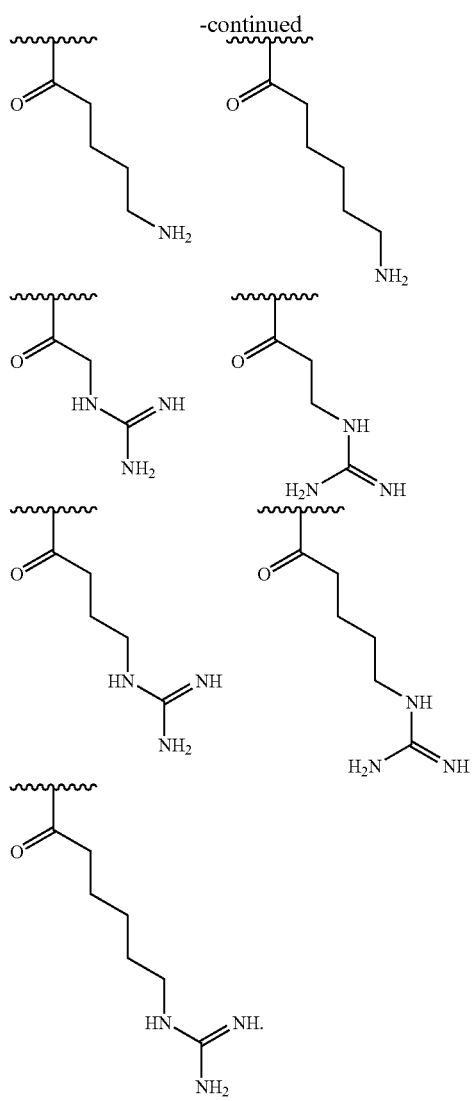

(E) Chitosan-Guanidine Compounds

In some embodiments, the present invention is directed to chitosan-guanidine compounds.

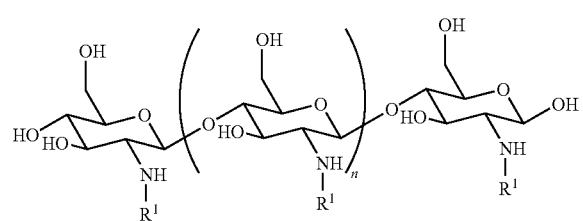

wherein each $R^1$ is independently selected from hydrogen, acetyl, and a group in which $R^1$, together with the nitrogen to which it is attached, forms a guanidine moiety; wherein at least 25% of $R^1$ substituents are H, at least 1% are acetyl, and at least 2% form a guanidine moiety together with the nitrogen to which it is attached.

(F) Neutral Chitosan Derivative Compounds

In some embodiments, the present invention is directed to neutral chitosan derivative compounds. Exemplary neutral chitosan derivative compounds include those where one or more amine nitrogens of the chitosan has been covalently attached to a neutral moiety such as a sugar:

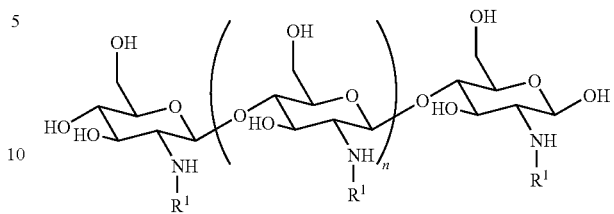

wherein each $R^1$ is independently selected from hydrogen, acetyl, and a sugar (e.g., a naturally occurring or modified sugar) or an α-hydroxy acid. Sugars can be monosaccharides, disaccharides or polysaccharides such as glucose, mannose, lactose, maltose, cellubiose, sucrose, amylose, glycogen, cellulose, gluconate, or pyruvate. Sugars can be covalently attached via a spacer or via the carboxylic acid, ketone or aldehyde group of the terminal sugar. Examples of α-hydroxy acids include glycolic acid, lactic acid, and citric acid. In some preferred embodiments, the neutral chitosan derivative is chitosan-lactobionic acid compound or chitosan-glycolic acid compound. Exemplary salts and coderivatives include those known in the art, for example, those described in US 2007/0281904, the contents of which is incorporated by reference in its entirety.

Treatment

As above, soluble chitosan or derivatized chitosan described herein can be used to treat bacteria infection and/or inhibit the growth of bacteria. The methods can be used to treat a subject.

The compounds described herein can be administered to cells in culture, e.g. in vitro or ex vivo, or to a subject, e.g., in vivo, or applied to an object to treat or prevent a variety of bacterial infection, including those described herein below. In some embodiments, the compounds and/or compositions inhibit the growth of bacteria and/or decrease bacterial load in a subject or on an object.

As used herein, the term "treat" or "treatment" is defined as the application or administration of a compound (e.g., a combination of compounds described herein) to a subject, e.g., a patient, or application or administration of the compound to an isolated tissue or cell, e.g., cell line, from a subject, e.g., a patient, who has a bacterial infection (e.g., a bacterial described herein) or a bacterial infection, with the purpose to cure, heal, alleviate, relieve, alter, remedy, ameliorate, improve or affect the bacterial infection, one or more symptoms of the bacterial infection or the predisposition toward the bacterial infection (e.g., to prevent at least one symptom of the bacterial infection or to delay onset of at least one symptom of the bacterial infection).

As used herein, an amount of a compound effective to treat a disorder, or a "therapeutically effective amount" refers to an amount of the compound which is effective, upon single or multiple dose administration to a subject, in treating a cell, or in curing, alleviating, relieving or improving a subject with a disorder beyond that expected in the absence of such treatment.

As used herein, an amount of a compound effective to prevent a bacterial infection, or a "a prophylactically effective amount" of the compound refers to an amount effective, upon single- or multiple-dose administration to the subject, in preventing or delaying the occurrence of the onset or recurrence of a disorder or a symptom of the bacterial infection.

As used herein, a "minimum inhibitory concentration (MIC)" is the lowest concentration of an anti-bacterial that inhibits the visible growth of a bacterium after overnight incubation. MIC can be used to confirm resistance of bacteria to an anti-bacterial agent and also to monitor the activity of new anti-bacterial agents. MIC can be determined by agar or broth dilution methods usually following the guidelines of a reference body such as the Clinical and Laboratory Standards Institute (CLSI), British Society for Antimicrobial Chemotherapy (BSAC) or The European Committee on Antimicrobial Susceptibility Testing (EUCAST). Methods to determine MIC are described, e.g., in Andrews J M. *Journal of Antimicrobial Chemotherapy* 48 (Suppl. 1):5-16, (2001).

In some embodiments, a soluble chitosan or chitosan derivative is administered to a subject in combination with an anti-bacterial agent. As used herein, "administered in combination" or a combined administration of two agents means that two or more agents (e.g., compounds described herein) are administered to a subject at the same time or within an interval such that there is overlap of an effect of each agent on the patient. Preferably they are administered within 15, 10, 5, or 1 minute of one another. Preferably the administrations of the agents are spaced sufficiently close together such that a combinatorial (e.g., a synergistic) effect is achieved. The agents can be administered simultaneously, for example in a combined unit dose (providing simultaneous delivery of both agents). Alternatively, the agents can be administered at a specified time interval, for example, an interval of minutes, hours, days or weeks. Generally, the agents are concurrently bioavailable, e.g., detectable, in the subject.

In a preferred embodiment, the agents are administered essentially simultaneously, for example two unit dosages administered at the same time, or a combined unit dosage of the two agents. In another preferred embodiment, the agents are delivered in separate unit dosages. The agents can be administered in any order, or as one or more preparations that includes two or more agents. In a preferred embodiment, at least one administration of one of the agents, e.g., the first agent, is made within minutes, one, two, three, or four hours, or even within one or two days of the other agent, e.g., the second agent. In some cases, combinations can achieve synergistic results, e.g., greater than additive results, e.g., at least 20, 50, 70, or 100% greater than additive.

In some embodiments the combination of a soluble chitosan or chitosan derivative and an antibacterial agent results in a reduction in Minimum Inhibitory Concentration (MIC) of the chitosan derivative of at least about 5% (e.g., at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99%, or at least about 99.5%. In some embodiments the combination results in a reduction in MIC of the anti-bacterial agent of at least about 5% (e.g., at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99%, or at least about 99.5%.

Derivatized chitosans described herein, such as chitosan derivatized with arginine, are generally active in the gut and do not cross into the bloodstream. However, the derivatized chitosan can also be used to enhance systemically administered drugs, e.g., an antibiotic such as tetracycline, that act at the epithelia so systemic treatments (of conditions like septicemia or Crohn's disease) can use less antibiotic than would be required in the absence of the derivatized chitosan.

Compositions and methods using a soluble chitosan or derivatized chitosan described herein can be used to treat a broad spectrum of pathogens, e.g., Gram-negative bacterial pathogens (e.g., *Escherichia coli, Pseudomonas aeruginosa, Pseudomonas fluorescens, Acinetobacter baumannii, Klebsiella pneumonia, Shigella flexneri, Salmonella typhi,* and *Proteus mirabilis*); and Gram-positive bacterial pathogens (e.g., *Bacillus subtilis, Staphylococcus aureus* (e.g., MRSA), *Staphylococcus epidermidis, Streptococcus mutans, Clostridium perfringens, Streptococcus pyogenes,* or *Enterococcus* (e.g., vancomycin resistant)).

Multiple Drug Resistance (MDR)

Compositions and methods useful for treating and/or inhibiting acquisition of a multiple drug resistance (MDR) bacteria are described herein. The composition and methods described herein can be used to treat a subject at risk for exposure to or infection with an MDR bacterium. Exemplary compositions and methods generally include use of a soluble chitosan or derivatized chitosan, including administering to a subject a soluble chitosan or derivatized chitosan described herein or a composition comprising a soluble chitosan or derivatized chitosan described herein to a subject having a multiple drug resistance (MDR) bacteria or at risk of having a multiple drug resistance (MDR) bacteria.

As used herein, "multiple drug resistance (MDR)" (also called multidrug resistance) is a condition enabling a disease-causing organism, e.g., bacteria, to no longer be killed or inhibited in growth by distinct drugs or chemicals, e.g., anti-bacterial agents in doses that are considered clinically relevant. Susceptibility and resistance to anti-bacterials are expressed as either a concentration or a zone diameter for growth inhibition. Clinical anti-bacterial "breakpoints" refer to the minimum inhibitory concentration (MIC) for a given anti-bacterial where there is a high likelihood of treatment failure, and are derived from human clinical studies or from knowledge derived from pharmacodynamic and pharmacokinetic techniques applied to animal models. A large number of national societies and organizations set these break-points using various standards, and include the Clinical and Laboratory Standards Institute (CLSI) and the Food and Drug Administration (FDA) in the US, the Swedish Reference Group for Antibiotics (SRGA), the Japanese Society for Chemotherapy (JSC) etc. [see John Turnidge and David Paterson, Clinical Microbiology Reviews Vol 20 (3), July 2007 pp. 391-408]

Bacteria can employ several mechanisms in attaining MDR, e.g., modification of specific targeted enzyme so it is not longer inactivated by the drug, enzymatic deactivation of antibiotics, decreased cell wall permeability to antibiotic, altered target sites of antibiotic, efflux mechanisms to remove antibiotics, etc. Increased mutation rate as a stress response is a common mechanism for variants in altered sites and enzymes to arise. Nearly all bacteria, e.g., *Staphylococci, Enterococci, Gonococci, Streptococci, Salmonella, Mycobacterium tuberculosis*, are able to exhibit MDR. Most bacteria, excluding *Mycobacteria*, have multiple routes for acquiring and disseminating resistance to a drug. Resistance is spread clonally as bacteria grow. Plasmids can be transferred by conjugation to other bacteria, such as within the Enterobacteriaecae (*E. Coli, Enterobacter* and *Citrobacter* species). Transposition of the resistance gene to other plasmids also increases the ability of the resistant gene to be transferred between different bacteria.

As used herein, "resistant microorganism or bacterium" means an organism which has become resistant to an antibacterial agent. In embodiments a the minimum inhibitory concentration of a resistant bacterium will be at least, 2, 5, 10, or 100 greater than for that seen with a non-resistant bacterium for a selected anti-bacterial agent.

As used herein, "resistance breakpoint" is the threshold concentration of an antibacterial agent above which a bacterium is considered resistant as defined above.

Mechanisms of Resistance

Four common mechanisms by which microorganisms exhibit resistance to antimicrobials are:

1. Drug inactivation or modification: e.g. enzymatic deactivation of beta-lactams in some Penicillin-resistant bacteria occurs through the production of β-lactamases which destroy the active part of the lactam. Vancoymycin resistance is typically the enzymatic removal of the last two peptides of the chain reducing its activity ~1000 times.

2. Alteration of drug target site: The bacterium produces a modified protein or enzyme that binds to the drug, rendering it ineffective. For example, penicillin-binding proteins (PBP's) bind to beta-lactam antibiotics blocking their inhibition of cell wall construction. The drug can no longer act at the intended site.

3. Alteration of metabolic pathway: The bacteria utilize alternative pathways that bypass the metabolic pathway that the drug affects. For example, sulfanamides inhibit the synthesis of folic acid early in the bacterial metabolic pathway. Some sulfonamide-resistant bacteria, like *mammalian* cells, turn to utilizing preformed folic acid from a different pathway that is not affected by the sulfanamide.

4. Efflux pumps: Bacteria reduce drug accumulation by increasing active efflux (pumping out) of the drugs across the cell surface. The resistant bacteria can also reduce drug accumulation by decreasing drug permeability into the cell and/or its interaction once inside. (Efflux pumps are common mechanisms for ciprofloxacin and silver)

In some embodiments, a soluble chitosan or chitosan derivative described herein, can prevent or overcome one or more of these mechanisms described above (e.g., when administered to a subject having a bacterial infection or contacting a bacteria).

Exemplary MDR pathogens, together with drugs typically used to treat infections of that pathogen and typical locations of infection are shown in Table 1A below.

TABLE 1A

MDR bacteria effectively treated with chitosan-arginine
Human

| Bacteria | Drugs tested | Typical infectious locations |
| --- | --- | --- |
| MRSA and human clinical isolates | Methicillin, Oxacillin, Penicillins, whole class of beta lactams | Nosocomial infections, wounds, pulmonary, flesh, bacteremia |
| *Acinetobacter baumannii* | Ampicillin, Tetracycline, Naladixic acid, Ticarcillin, Trimethoprim, Sulfamethoxazole, Cefotaxime, Ciprofloxacin, Cefazolin, Cefazidime, Cefuroxime, Cefepime, Imipenem, Mezlocillin, Piperacillin, Gentamicin, and Levofloxacin | Wounds, pulmonary, nosocomial infections |
| *Kelbsiella pneumoniae* | Ampicillin, Streptomycin, Tetracycline, Naladixic acid, Ticarcillin, Trimethoprim, Sulfamethxazole, Cefotaxime, and Gentamicin | Respiratory pneumonia, bronchitis, urinary tract infections, bacteremia |
| MMRSA | Mupirocin and Methicillin resistant (Penicillins) | Wounds, lungs, flesh, bacteremia |
| VRE Vancoymicn resistant *Enterococcus faecium* | Vancomycin and others | Gastrointesitinal infections, and in particular *C. Difficile*, Vancomycin is toxic to humans at anything but lowest doses |
| *Pseudomonas aeruginosa*, clinical isolates | Aminoglycosides (Gentamicin, Tobramycin), | Wound infections, pulmonary infections, cystic fibrosis |
| *Salmonella enterica* | Ampicillin, chloramphenicol, streptomycin, sulfonamide, tetracycline | Gastrointestinal infections |

Synergy

In some embodiments a soluble chitosan or derivatized chitosan can be used in combination with an anti-bacterial agent to treat a bacterial infection and/or inhibit the growth of bacteria. For example, a soluble chitosan or derivatized chitosan can be administered to a subject in combination with an anti-bacterial agent to to treat a bacterial infection and/or inhibit the growth of bacteria. The combinations of a soluble chitosan or derivatized chitosan and an antibacterial agent can result in a synergistic effect, e.g., a reduced minimum inhibitory concentration (MIC) of both the soluble chitosan or chitosan derivative, and the antibacterial agent, so that the effect is greater than the sum of the effects. The combinations of a soluble chitosan or derivatized chitosan and an antibacterial agent can result in a synergistic bactericidal effect. The effect of treatment of bacteria with combinations of soluble chitosan or chitosan derivative and the antibacterial at that dose is measured. If the combination results in a reduction of viable bacteria that is two logs greater than the most effective individual components, the combination is considered synergistic.

The term "synergy" or "synergistic" as used herein, refers to an outcome when two agents are used in combination, wherein the combination of the agents acts so as to require a smaller amount of each individual agent than that agent would require to be efficacious in the absence of the other agent, for example, with lower dosages of the first agent than would be required in the absence of the second agent. In some embodiments, use of synergistic agents can result in the beneficial effect of less overall use of an agent.

For example, the fractional inhibitory concentration (FIC) is one type of measure of the interaction of two agents, such as an antibiotic and a chitosan derivative, used together, and is a powerful indicator of synergy. FIC uses the minimum inhibitory concentrations (MIC's) of each of the independent agents, A and B, for a particular bacterium as the basis, MIC(A) and MIC(B). Then takes the concentration of each component in a mixture where an MIC is observed, so for a two component system of A and B, MIC (A in B) is the concentration of A in the compound mixture and MIC (B in A) is the concentration of B in the mixture.

The FIC is defined as follows:
FIC=MIC(A in B)/MIC(A)+MIC (B in A)/MIC(B)
If FIC< or =0.5, the mixture is synergistic
If FIC=1, the mixture is additive
If FIC>4 the mixture is antagonistic
For example say A=chitosan-arginine and B=ciprofloxacin
Against *Pseudomonas aeruginosa*,
Alone MIC(A)=8 µg/ml
MIC(B)=0.5 µg/ml
For example 1:
A combination of 1 µg/ml A with 0.1 µg/ml of B, resulting in the killing of bacteria FIC=1/8+0.1/0.5=0.325, and is considered synergistic
For example 2:
Note that if half and half are used, it is additive, for example
A combination of 4 µg/ml A with 0.25 µg/ml of B, resulting in the killing of bacteria (FIC)=4/8+0.25/0.5=0.5+0.5=1

For instances where bactericidal activity, rather than inhibitory activity is measured, a time kill assay is used. A minimum bactericida concentration (MBC) can be determined for a given period of time, and with a cut off of 3 or 4 or 5 log reduction in viable bacteria. For the purposes of defining synergy in a time kill assay, a combination of treatments is considered synergistic if the resultant bactericidal activity is 2 logs more effective than the most effective individual activity. [Stratton, C. W. & Cooksey, R. C. (1991). Susceptibility tests: special tests. In *Manual of Clinical Microbiology* (Balows, A., Ed.), pp. 1153-65. American Society Microbiology, Washington D.C.]

In some embodiments the combination results in a reduction in MIC or MBC of the soluble chitosan or chitosan derivative of at least about 5% (e.g., at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99%, or at least about 99.5%. In some embodiments the combination results in a reduction in MIC of the antibacterial agent of at least about 5% (e.g., at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99%, or at least about 99.5%.

In some embodiments the combination results in a Fractional Inhibitory Concentration (FIC) of the chitosan derivative and the anti-bacterial agent less than about 0.5 (e.g., less than about 0.4, less than about 0.3, less than about 0.2, less than about 0.1, less than about 0.05, less than about 0.02, less than about 0.01, less than about 0.005, less than about 0.001)

In some embodiments, the combination results in a bactericidal activity at least about 2, 2.5, 3, 3.5, 4, 4.5, or 5 logs more effective than the most effective individual activity, e.g., the activity of the chitosan derivative or the anti-bacterial agent.

Mechanisms of Antibacterials

Compositions and methods using a soluble chitosan or deriviatized chitosan described herein and an antibacterial agent can be used to treat bacterial infection and/or inhibit the growth of bacteria. The combinations of a soluble chitosan or derivatized chitosan described herein and an antibacterial agent can result in a synergistic effect, e.g., a reduced minimum inhibitory concentration (MIC) of either the soluble chitosan or chitosan derivative, or the antibacterial agent, or both.

Antibacterial action generally falls within one of four mechanisms, three of which involve the inhibition or regulation of enzymes involved in cell wall biosynthesis, nucleic acid metabolism and repair, or protein synthesis. The fourth mechanism involves the disruption of membrane structure, like a pore-former. A common example of a pore-former is polymixin B.

Many of these cellular functions targeted by antibiotics are most active in multiplying cells. Such cells are often rapidly dividing as are cancer cells and some antibacterials have also been found to be useful as anticancer agents.

Some antibacterials inhibit an enzyme necessary for bacterial survival or replication or block an enzymes binding site without contacting the enzyme specifically. These typically are found to interfere with cell wall synthesis, interfere with DNA synthesis, or interfere with protein synthesis. The latter mechanisms are disruption of a cell membrane, causing leakage, disruption of osmotic gradients, and loss of critical cellular contents.

General Classes of Antibacterials and Mechanisms (a Star Indicates the Antibacterial has been Tested and Shows Synergy)

Aminoglycosides: Inhibit protein synthesis by binding to a portion of the bacterial ribosome. Most of them are bactericidal (i.e., cause bacterial cell death).

Bacitracin: Inhibits cell wall production by blocking the step in the process (recycling of the membrane lipid carrier) which is needed to add on new cell wall subunits.

Beta-lactam antibiotics: Antibiotics in this group contain a specific chemical structure (i.e., a beta-lactam ring). This includes Penicillins, Cephalosporins, Carbapenems and Monobactams. They inhibit the synthesis of the peptidoglycan layer of bacterial cell walls of Gram-positive organisms, by binding to PBP, Penicillin binding protein that is the last step in cell wall synthesis. However, some Gram-negative organisms seem to be susceptible Cephalosporins: These are similar to Penicillins in their mode of action but they treat a broader range of bacterial infections. They have structural similarities to Penicillins and many people with allergies to Penicillins also have allergic reactions to Cephalosporins.

Chloramphenicol: Inhibits protein synthesis by binding to a subunit of bacterial ribosomes (50S).

Glycopeptides (e.g., Vancomycin): Interferes with cell wall development by blocking the attachment of new cell wall subunits (muramyl pentapeptides). Macrolides (e.g., Erythromycin) and Lincosamides (e.g., Clindamycin): Inhibit protein synthesis by binding to a subunit of the bacterial ribosome (50S).

Penicillins: Inhibit formation of the bacterial cell wall by blocking cross-linking of the cell wall structure. The cell wall is a needed protective casing for the bacterial cell.

Quinolones: Blocks DNA synthesis by inhibiting one of the enzymes (DNA gyrase) needed in this process. (Ciprofloxacin is a fluoroquinolone)

Rifampin: Inhibits RNA synthesis by inhibiting one of the enzymes (DNA-dependent RNA polymerase) needed in this process. RNA is needed to make proteins.

Glycopeptide: Like Vancoymcin, inhibits cell wall synthesis.

Tetracyclines: Inhibit protein synthesis by binding to the subunit of the bacterial ribosome (30S subunit).

Trimethoprim and Sulfonamides: Blocks cell metabolism by inhibiting enzymes which are needed in the biosynthesis of folic acid which is a necessary cell compound.

Exemplary antibiotics are provided as follows. Exemplary aminoglycosides include Streptomycin, Neomycin, Framycetin, Parpmycin, Ribostamycin, Kanamycin, Amikacin, Dibekacin, Tobramycin, Hygromycin B, Spectinomycin, Gentamicin, Netilmicin, Sisomicin, Isepamicin, Verdamicin, Amikin, Garamycin, Kantrex, Netromycin, Nebcin, and Humatin. Exemplary carbacephems include Loracarbef (Lorabid). Exemplary carbapenems include Ertapenem, Invanz, Doripenem, Finibax, Imipenem/Cilastatin, Primaxin, Meropenem, and Merrem. Exemplary cephalosporins include Cefadroxil, Durisef, Cefazolin, Ancef, Cefalotin, Cefalothin, Keflin, Cefalexin, Keflex, Cefaclor, Ceclor, Cefamandole, Mandole, Cefoxitin, Mefoxin, Cefprozill, Cefzil, Cefuroxime, Ceftin, Zinnat, Cefixime, Suprax, Cefdinir, Omnicef, Cefditoren, Spectracef, Cefoperazone, Cefobid, Cefotaxime, Claforan, Cefpodoxime, Fortaz, Ceftibuten, Cedax, Ceftizoxime, Ceftriaxone, Rocephin, Cefepime, Maxipime, and Ceftrobriprole. Exemplary glycopeptides include Dalbavancin, Oritavancin, Teicoplanin, Vancomycin, and Vancocin. Exemplary macrolides include Azithromycin, Sithromax, Sumamed, Zitrocin, Clarithromycin, Biaxin, Dirithromycin, Erythromycin, Erythocin, Erythroped, Roxithromycin, Troleandomycin, Telithromycin, Ketek, and Spectinomycin. Exemplary monobactams include Aztreonam. Exemplary penicillins include Amoxicillin, Novamox, Aoxil, Ampicillin, Azlocillin, Carbenicillin, Coxacillin, Diloxacillin, Flucloxacillin Floxapen, Mezlocillin, Methicillin, Nafcillin, Oxacillin, Penicillin, and Ticarcillin Exemplary polypeptides include Bacitracin, Colistin, and Polymyxin B. Exemplary quinolones include Ciprofloxacin, Cipro, Ciproxin, Ciprobay, Enoxacin, Gatifloxacin, Tequin, Levofloxacin, Levaquin, Lomefloxacin, Moxifloxacin, Avelox, Norfloxacin, Noroxin, Ofloxacin, Ocuflox, Trovafloxacin, and Trovan. Exemplary sulfonamides include Mefenide, Prontosil (archaic), Sulfacetamide, Sulfamethizole, Sulfanilamide (archaic), Sulfasalazine, Sulfisoxazole, Trimethoprim, Trimethoprim-Sulfamethoxazole (co-trimoxazole), and Bactrim. Exemplary tetracyclines include Demeclocycline, Doxycycline, Vibramycin, Minocycline, Minocin, Oxytetracycline, Terracin, Tetracycline, and Sumycin. Other exemplary antibiotics include Salvarsan, Chloamphenicol, Chloromycetin, Clindamycin, Cleocin, Linomycin, Ethambutol, Fosfomycin, Fusidic Acid, Fucidin, Furazolidone, Isoniazid, Linezolid, Zyvox, Metronidazole, Flagyl, Mupirocin, Bactroban, Nitrofurantion, Macrodantin, Macrobid, Platensimycin, Pyrazinamide, Quinupristin/Dalfopristin (Syncerid), Rifampin (rifampicin), and Tinidazole.

Methods and compositions using a soluble chitosan or derivatized chitosan described herein and an antibacterial agent are useful for inhibiting the growth of a broad spectrum of pathogens. The combinations of a soluble chitosan or derivatized chitosan and an antibacterial agent can result in a synergistic effect, e.g., a reduced minimum inhibitory concentration (MIC) of either the soluble chitosan or chitosan derivative, or the antibacterial agent, or both. Exemplary pathogens, together with drugs typically used to treat infections of that pathogen and typical locations of infection are shown in Table 1B below.

TABLE 1B

Pathogens Tested for Synergy with Chitosan-arginine (and their clinical infectious locations)
Human

| Bacteria | Drugs tested | Typical infectious locations |
| --- | --- | --- |
| Pseudomonas aeruginosa | Ciprofloxacin, Rifampicin, Neomycin, silver and Gentamicin | Wounds, lungs, respiratory, bacterimia |
| Staphylococcus aureus | Silver | Wounds, lungs, flesh, bacteremia, nosocomial infections |
| E. coli | Silver, Ciprofloxacin | Gastrointestinal |
| Streptococcus pneumoniae | Silver | Respiratory |
| Burkolderia cepacia | Silver | Respiratory |

Other exemplary pathogens include: bacteria such as Streptococcus pneumoniae, Streptococcus pyogenes, Enterococcus faecalis, Enterococcus faecium, Klebsiella pneumoniae, Enterobacter sps., Proteus sps., Pseudomonas aeruginosa, E. coli, Serratia marcesens, Staphylococcus aureus, Coag. Neg. Staph, Haemophilus influenzae, Bacillus anthracia, Mycoplasma pneumoniae, Moraxella catarralis, Chlamydia pneumoniae, Legionella pneumophila, Mycobacterium tuberculosis, Staphylococcus epidermidis, or Helicobacter pylori.

Other exemplary pathogens include the following, which can be susceptible and/or resistant forms of the following; Methicillin resistant Staphylococcus aureus, Mupirocin resistant Staphylococcus aureus, Mupirocin and Methicillin resistant Staphylococcus aureus, Fluoroquinolone resistant Staphylococcus aureus, Vancomycin intermediate resistant Staphylococcus aureus, Linezolid resistant Staphylococcus aureus, Penicillin resistant Streptococcus pneumoniae, Macrolide resistant Streptococcus pneumoniae, Fluoroquinolone resistant Streptococcus pneumoniae. Vancomycin resistant Enterococcus faecalis, Linezolid resistant Enterococcus faecalis, Fluoroquinolone resistant Enterococcus faecalis, Vancomycin resistant Enterococcus faecium, Linezolid resistant Enterococcus faecium. Fluoroquinolone resistant Enterococcus faecium, Ampicillin resistant Enterococcus faecium, Macrolide resistant Haemophilus influenzae, β-lactam resistant Haemophilus influenzae, Fluoroquinolone resistant Haemophilus influenzae, β-lactam resistant Moraxella catarrhalis, Methicillin resistant Staphylococcus

*epidermidis*, Methicillin resistant *Staphylococcus epidermidis*, Vancomycin resistant *Staphylococcus epidermidis*, Fluoroquinolone resistant *Staphylococcus epidermidis*, Macrolide resistant *Mycoplasma pneumoniae*, Isoniazid resistant *Mycobacterium tuberculosis*, Rifampin resistant *Mycobacterium tuberculosis*, Methicillin resistant coagulase negative *Staphylococci*, Fluoroquinolone resistant coagulase negative *Staphylococci*, Glycopeptide intermediate resistant *Staphylococcus aureus*, Vancomycin resistant *Staphylococcus aureus*, Hetero vancomycin intermediate resistant *Staphylococcus aureus*, Hetero vancomycin resistant *Staphylococcus aureus*, Macrolide-Lincosamide-Streptogramin resistant *Staphylococcus*, β-lactam resistant *Enterococcus faecalis*, β-lactam resistant *Enterococcus faecium*, Ketolide resistant *Streptococcus pneumoniae*, Ketolide resistant *Streptococcus pyogenes*, Macrolide resistant *Streptococcus pyogenes*, or Vancomycin resistant *Staphylococcus epidermidis*.

Sensitization

In some embodiments a soluble chitosan or derivatized chitosan can be used in combination with an anti-bacterial agent to treat and/or inhibit a resistant bacterial infection and/or the growth of resistant bacterial infection, e.g., by sensitizing a bacterium that was previously resistant to an antibacterial agent. Sensitization is the process of reducing the MIC of an antibiotic for resistant bacteria to a value that is below the resistance breakpoint, thereby rendering the bacteria susceptible to that antibiotic. The compounds and compositions can be used to treat a subject having resistant bacterial infection (e.g., by administering a soluble chitosan or derivatized chitosan in combination with an anti-bacterial agent. The combinations of a soluble chitosan or derivatized chitosan and an antibacterial agent can result in sensitization of a resistant bacterium, e.g., the resistant bacterium has a reduced minimum inhibitory concentration (MIC) of either the soluble chitosan or chitosan derivative, or the antibacterial agent, or both, so that the MIC is below the resistance breakpoint.

As used herein, rendering or transforming a resistant bacterium into a sensitive bacterium means reducing the minimum inhibitory concentration (MIC), e.g., by at least 2, 4, 10, or 100 fold.

As used herein "resistant microorganism or bacterium" means an organism which has become resistant to an anti-bacterial agent, e.g. having an MIC that is greater than the resistance breakpoint (as defined above). In embodiments a the minimum inhibitory concentration (MIC) of a resistant bacterium will be at least, 2, 5, 10, or 100 greater than for that seen with a non-resistant bacterium for a selected anti-bacterial agent.

In some embodiments the combination results in a reduction in MIC of the chitosan derivative of at least about 5% (e.g., at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99%, or at least about 99.5%. In some embodiments the combination results in a reduction in MIC of the anti-bacterial of at least about 5% (e.g., at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99%, or at least about 99.5%.

In some embodiments the combination results in a Fractional Inhibitory Concentration (FIC) of the chitosan derivative and the anti-bacterial agent less than about 0.5 (e.g., less than about 0.4, less than about 0.3, less than about 0.2, less than about 0.1, less than about 0.05, less than about 0.02, less than about 0.01, less than about 0.005, less than about 0.001)

In some embodiments, the combination results in a bactericidal activity at least about 2, 2.5, 3, 3.5, 4, 4.5, or 5 logs more effective than the most effective individual activity, e.g., the activity of the chitosan derivative or the anti-bacterial agent.

The term "resistant breakpoint" is defined herein in the section of "Multiple Drug Resistance (MDR)". The mechanisms of resistance are described herein in the section of "Multiple Drug Resistance (MDR)". The mechanisms of antibacterials and general classes of antibacterials and mechanisms are described herein in the section of "Synergy".

Compositions and methods described herein are useful for inhibiting resistant bacterial infection and/or the growth of resistant bacterial infection, e.g., by sensitizing a bacterium that was previously resistant to an antibacterial agent. Exemplary compositions and methods generally include use of a soluble chitosan or derivatized chitosan and an antibacterial agent. The combinations of a soluble chitosan or derivatized chitosan and an antibacterial agent can result in sensitization of a resistant bacterium, e.g., a reduced minimum inhibitory concentration (MIC) of either the soluble chitosan or chitosan derivative, or the antibacterial agent, or both. Exemplary resistant bacteria, together with drugs typically used to treat infections of that pathogen and typical locations of infection are shown in Table 1C below:

TABLE 1C

Important Pathogens for Sensitization by chitosan-arginine Human

| Bacteria | Drugs tested | Typical infectious locations |
| --- | --- | --- |
| MRSA | Resistant to Methicillin, Oxicillin, other Penicillins | Key player in nosocomial infections in the US |
| VRE (vancomycin resistant enterococcus faecium) | Resistant to Vancomycin | Primary infectious *enterococcus* in hospitals |
| MMRSA | Resistant to all MRSA drugs as well as Mupirocin | Emerging resistant MRSA that is also mupirocin resistant (M-MRSA) |
| E Coli* | Somewhat resistant to Chitosan-arginine, but sensitized by Ciprofloxacin | *E. coli* is everywhere, but most known for gastrointestinal infections |
| *Clostridium difficile* | Vancomycin, Metronidazole, Teicoplanin, Fusidin | Not yet tested for sensitization |

*C/A has a high MIC on *E. Coli*; sensitization lowers both the dose of chitosan-arginine and ciprofloxacin at least an order of magnitude each.

Other exemplary pathogens also include bacteria that cause resistant bacterial infections such as Methicillin resistant *Staphylococcus aureus*, Mupirocin resistant *Staphylococcus aureus*, Mupirocin and Methicillin resistant *Staphylococcus aureus*, Fluoroquinolone resistant *Staphylococcus aureus*, Vancomycin intermediate resistant *Staphylococcus aureus*, Linezolid resistant *Staphylococcus aureus*, Penicillin resistant *Streptococcus pneumoniae*, Macrolide resistant *Streptococcus pneumoniae*, Fluoroquinolone resistant *Streptococcus pneumoniae*. Vancomycin resistant *Enterococcus faecalis*, Linezolid resistant *Enterococcus faecalis*, Fluoroquinolone resistant *Enterococcus faecalis*, Vancomycin resistant *Enterococcus faecium*, Linezolid resistant *Enterococcus*

*faecium*. Fluoroquinolone resistant *Enterococcus faecium*, Ampicillin resistant *Enterococcus faecium*, Macrolide resistant *Haemophilus influenzae*, β-lactam resistant *Haemophilus influenzae*, Fluoroquinolone resistant *Haemophilus influenzae*, β-lactam resistant *Moraxella catarrhalis*, Methicillin resistant *Staphylococcus epidermidis*, Methicillin resistant *Staphylococcus epidermidis*, Vancomycin resistant *Staphylococcus epidermidis*, Fluoroquinolone resistant *Staphylococcus epidermidis*, Macrolide resistant *Mycoplasma pneumoniae*, Isoniazid resistant *Mycobacterium tuberculosis*, Rifampin resistant *Mycobacterium tuberculosis*, Methicillin resistant coagulase negative *Staphylococci*, Fluoroquinolone resistant coagulase negative *Staphylococci*, Glycopeptide intermediate resistant *Staphylococcus aureus*, Vancomycin resistant *Staphylococcus aureus*, Hetero vancomycin intermediate resistant *Staphylococcus aureus*, Hetero vancomycin resistant *Staphylococcus aureus*, Macrolide-Lincosamide-Streptogramin resistant *Staphylococcus*, β-lactam resistant *Enterococcus faecalis*, β-lactam resistant *Enterococcus faecium*, Ketolide resistant *Streptococcus pneumoniae*, Ketolide resistant *Streptococcus pyogenes*, Macrolide resistant *Streptococcus pyogenes*, or Vancomycin resistant *Staphylococcus epidermidis*.

Subjects

Compositions and methods using a soluble chitosan or derivatized chitosan described herein can be used to treat a subject, e.g., a subject having bacterial infection. The subject can be a human or an animal. Suitable animal subjects include: but are not limited to, pet, wild, zoo, laboratory, and farm animals. Suitable animal subjects include primates, rodents, and birds. Examples of said animals include, but not limited to, guinea pigs, hamsters, gerbils, rat, mice, rabbits, dogs, cats, horses, pigs, sheep, cows, goats, deer, rhesus monkeys, monkeys, tamarinds, apes, baboons, gorillas, chimpanzees, orangutans, gibbons, fowl, e.g., pheasant, quail (or other gamebirds), a waterfowl, ostriches, chickens, turkeys, ducks, and geese or free flying bird.

Exemplary disorders in humans and animals include: those described above, for example as caused by an infection with a bacteria described above.

Exemplary disorders in humans and animals include diseases characterized by the presence of one or more of the following: bacteria such as *Streptococcus pneumoniae, Streptococcus pyogenes, Enterococcus faecalis, Enterococcus faecium, Klebsiella pneumoniae, Enterobacter* sps., *Proteus* sps., *Pseudomonas aeruginosa, E. coli, Serratia marcesens, Staphylococcus aureus*, Coag. Neg. *Staph, Haemophilus influenzae, Bacillus anthracia, Mycoplasma pneumoniae, Moraxella catarralis, Chlamydia pneumoniae, Legionella pneumophila, Mycobacterium tuberculosis, Staphylococcus epidermidis*, or *Helicobacter pylori*.

Exemplary disorders in humans and animals also include diseases characterized by the presence of one or more of the following: bacteria that cause resistant bacterial infections such as Methicillin resistant *Staphylococcus aureus*, Mupirocin resistant *Staphylococcus aureus*, Mupirocin and Methicillin resistant *Staphylococcus aureus*, Fluoroquinolone resistant *Staphylococcus aureus*, Vancomycin intermediate resistant *Staphylococcus aureus*, Linezolid resistant *Staphylococcus aureus*, Penicillin resistant *Streptococcus pneumoniae*, Macrolide resistant *Streptococcus pneumoniae*, Fluoroquinolone resistant *Streptococcus pneumoniae*. Vancomycin resistant *Enterococcus faecalis*, Linezolid resistant *Enterococcus faecalis*, Fluoroquinolone resistant *Enterococcus faecalis*, Vancomycin resistant *Enterococcus faecium*, Linezolid resistant *Enterococcus faecium*. Fluoroquinolone resistant *Enterococcus faecium*, Ampicillin resistant *Enterococcus faecium*, Macrolide resistant *Haemophilus influenzae*, β-lactam resistant *Haemophilus influenzae*, Fluoroquinolone resistant *Haemophilus influenzae*, β-lactam resistant *Moraxella catarrhalis*, Methicillin resistant *Staphylococcus epidermidis*, Methicillin resistant *Staphylococcus epidermidis*, Vancomycin resistant *Staphylococcus epidermidis*, Fluoroquinolone resistant *Staphylococcus epidermidis*, Macrolide resistant *Mycoplasma pneumoniae*, Isoniazid resistant *Mycobacterium tuberculosis*, Rifampin resistant *Mycobacterium tuberculosis*, Methicillin resistant coagulase negative *Staphylococci*, Fluoroquinolone resistant coagulase negative *Staphylococci*, Glycopeptide intermediate resistant *Staphylococcus aureus*, Vancomycin resistant *Staphylococcus aureus*, Hetero vancomycin intermediate resistant *Staphylococcus aureus*, Hetero vancomycin resistant *Staphylococcus aureus*, Macrolide-Lincosamide-Streptogramin resistant *Staphylococcus*, β-lactam resistant *Enterococcus faecalis*, β-lactam resistant *Enterococcus faecium*, Ketolide resistant *Streptococcus pneumoniae*, Ketolide resistant *Streptococcus pyogenes*, Macrolide resistant *Streptococcus pyogenes*, Vancomycin resistant *Staphylococcus epidermidis*, multidrug resistant *Clostridium difficile*, multidrug resistant *Acinetibacter baumannii*, multidrug resistant *Kelbsiella pneumoniae*, or multidrug resistant *Escherichia coli*.

As used herein primary contact means that an individual is in direct physical contact with the subject or that they exchange bodily fluids, e.g., by drinking from the same cup. Secondary contact means that a first individual has primary contact with a second individual and the second individual has direct contact with the subject.

Compositions and Formulations

The compounds described herein can be formulated in a variety of manners, including for oral, or topical delivery (e.g., administered orally, parenterally, by inhalation spray, nebulizer, topically, rectally, nasally, buccally). Inclusion in feed, water or an inhaled formulation is particularly desirable for use with animals.

The compounds described herein (e.g., a derivatized chitosan or an antibacterial agent) can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.001 to about 100 mg/kg of body weight, e.g., between 0.001-1 mg/kg, 1-100 mg/kg, or 0.01-5 mg/kg, every 4 to 120 hours, e.g., about every 6, 8, 12, 24, 48, or 72 hours, or according to the requirements of the particular compound. The methods herein contemplate administration of an effective amount of compound or compound composition to achieve the desired or stated effect. Typically, the pharmaceutical compositions of this invention will be administered from about 1 to about 6 times per day. Alternatively, the compounds can be administered as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Alternatively, such preparations contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained. Patients may, however, require intermittent treatment on a long-term basis upon any recurrence of disease symptoms.

Pharmaceutical compositions of this invention comprise a compound of the formulae described herein or a pharmaceutically acceptable salt thereof; an additional compound including for example, a steroid or an analgesic; and any pharmaceutically acceptable carrier, adjuvant or vehicle. Alternate compositions of this invention comprise a compound described herein or a pharmaceutically acceptable salt thereof; and a pharmaceutically acceptable carrier, adjuvant or vehicle. The compositions delineated herein include the compounds described herein, as well as additional therapeutic compounds if present, in amounts effective for achieving a modulation of disease or disease symptoms.

The compositions are generally made by methods including the steps of combining a compound described herein with one or more carriers and, optionally, one or more additional therapeutic compounds delineated herein.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound.

The pharmaceutical compositions of this invention may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase which can be combined with emulsifying and/or suspending agents. If desired, certain sweetening and/or flavoring and/or coloring agents may be added.

The compounds of this invention may be administered by aerosol, nebulizer, or inhalation. In some embodiments, the composition is in the form of a dry powder, a suspension, or a solution. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. Exemplary methods and devices for aerosol or inhalation include those described in U.S. Pat. No. 6,962,151, which is incorporated herein by reference in its entirety.

Compositions formulated for inhaled delivery generally include particles having a mean diameter of from about 0.1 μm to about 50 μm (e.g., from about 0.1 μm to about 10 μm, or from about 0.2 μm to about 5 μm. In some embodiments, the composition includes a dispersion of suitably-sized dry particles, for example, precipitants or crystals) or a dispersion of a solution (e.g., droplets) of a suitable size.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α, β-, and γ-cyclodextrin, may also be advantageously used to enhance delivery of compounds of the formulae described herein.

In some cases, the pH of the formulation may be adjusted with pharmaceutically acceptable acids, bases or buffers to enhance the stability of the formulated compound or its delivery form.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

When the compositions of this invention comprise a combination of compounds described herein, both the compounds are generally present at dosage levels of between about 1 to 100%, and more preferably between about 5 to 95% of the dosage normally administered in a monotherapy regimen. Additionally, combinations of a plurality of compounds described herein are also envisioned. The compounds may be administered separately, as part of a multiple dose regimen, from the compounds of this invention. Alternatively, those compounds may be part of a single dosage form, mixed together with the compounds of this invention in a single composition.

Kits

A compound described herein can be provided in a kit. The kit includes (a) a composition that includes a compound described herein, and, optionally (b) informational material. The informational material can be descriptive, instructional, marketing or other material that relates to the methods described herein and/or the use of the compound described herein for the methods described herein.

The informational material of the kits is not limited in its form. In one embodiment, the informational material can include information about production of the compound, molecular weight of the compound, concentration, date of expiration, batch or production site information, and so forth.

In one embodiment, the informational material relates to use of the compound described herein to treat a disorder described herein.

In one embodiment, the informational material can include instructions to administer the compound described herein in a suitable manner to perform the methods described herein, e.g., in a suitable dose, dosage form, or mode of administration (e.g., a dose, dosage form, or mode of administration described herein). Preferred doses, dosage forms, or modes of administration are parenteral, e.g., intravenous, intramuscular, subcutaneous, intraparenteral, bucosal, sublingual, intraoccular, and topical. In another embodiment, the informational material can include instructions to administer the compound described herein to a suitable subject, e.g., a human, e.g., a human having or at risk for a disorder described herein. For example, the material can include instructions to administer the compound described herein to such a subject.

The informational material of the kits is not limited in its form. In many cases, the informational material, e.g., instructions, is provided in printed matter, e.g., a printed text, drawing, and/or photograph, e.g., a label or printed sheet. However, the informational material can also be provided in other formats, such as computer readable material, video recording, or audio recording. In another embodiment, the informational material of the kit is contact information, e.g., a physical address, email address, website, or telephone number, where a user of the kit can obtain substantive information about an compound described herein and/or its use in the methods described herein. Of course, the informational material can also be provided in any combination of formats.

In addition to a compound described herein, the composition of the kit can include other ingredients, such as a solvent or buffer, a stabilizer, a preservative, and/or a second compound for treating a condition or disorder described herein. Alternatively, the other ingredients can be included in the kit, but in different compositions or containers than the compound described herein. In such embodiments, the kit can include instructions for admixing the compound described herein and the other ingredients, or for using a compound described herein together with the other ingredients.

The compound described herein can be provided in any form, e.g., liquid, dried or lyophilized form. It is preferred that the compound described herein be substantially pure and/or sterile. When the compound described herein is provided in a liquid solution, the liquid solution preferably is an aqueous solution, with a sterile aqueous solution being preferred. When the compound described herein is provided as a dried form, reconstitution generally is by the addition of a suitable solvent. The solvent, e.g., sterile water or buffer, can optionally be provided in the kit.

The kit can include one or more containers for the composition containing the compound described herein. In some embodiments, the kit contains separate containers, dividers or compartments for the composition and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of a compound described herein. For example, the kit includes a plurality of syringes, ampules, foil packets, or blister packs, each containing a single unit dose of a compound described herein.

The containers of the kits can be air tight, waterproof (e.g., impermeable to changes in moisture or evaporation), and/or light-tight.

The kit optionally includes a device suitable for administration of the composition, e.g., a syringe, inhalant, pipette, forceps, measured spoon, dropper (e.g., eye dropper), swab (e.g., a cotton swab or wooden swab), or any such delivery device. In a preferred embodiment, the device is an implantable delivery device.

EXAMPLES

Example 1

Inhibition of Plasmid Transformation by Chitosan-Arginine

Plasmids containing genes conferring resistance to a drug can be taken up by bacteria, and those bacteria become drug resistant. Chitosan-arginine prevents the spread of antibiotic resistance by interfering with this horizontal gene transfer.

The pUC19 plasmid DNA confers resistance to Ampicillin. The plasmid was transformed into *E. coli* FB5a (Fisher) competent cells via heat shock. Control *E. coli* which had not been transformed were all killed by the placement of the bacteria on agar plates supplemented with 100 µg/mL of Ampicillin Cells that had been transformed were resistant and did not die. Control cells were not resistant and did die.

In this study, chitosan-arginine was added at various times in the transformation cycle to demonstrate where the chitosan-arginine interacts with the plasmid. The control experiment utilized 50 pg of pUC19 plasmid in 5 µL DNA in water. The plasmid was added to 100 µL of *E. coli* FB5a competent cells and incubated on ice for 20 minutes. Transformation occurred via heat shock for 45 seconds followed by addition of 1 ml of LB broth and incubated at 37° C. for 1 hour before being plated for recover colony forming units (cfu).

The experiment mixed 50 pg of the pUC19 plasmid in 5 µL water with 5 µL 250 ng of chitosan-arginine (37%, 40 kDa, 2.45 PDI, 89% DDA). The pUC19 plasmid pre-treated with chitosan-arginine was added to 100 µL of *E. coli* FB5a competent cells and transformation occurred via standard heat shock and recovery technique. The cells were plated out, however no cfu were recovered, showing complete inhibition of plasmid transformation (i.e. no transfer of resistance). (chitosan-arginine+plasmid)

Additional experiments were controls to test for the effect of chitosan-arginine presence during the transformation process at time following plasmid contact with cells. The inventors observed that the addition of chitosan-arginine after heat shock or during or directly after the recovery phase had no significant affect on the transformation efficiency (p≥0.32). The addition of chitosan-arginine before the heat shock step resulted in a significant reduction of transformation efficiency (approximately 1-log, p=0.05). No transformation occurred when chitosan-arginine was preincubated with the plasmid before exposure to the cells. Chitosan-arginine prevented the transfer of a resistance gene to *E. Coli*.

The results of this study are shown in FIG. 1.

Multiple hypotheses could contribute to the mechanisms of MDR and resistance prevention, e.g., metabolism hypothesis, and DNA binding or interference hypothesis for transfer of resistance (conjugation hypothesis, and phage transmission of DNA through receptors). Prevention of resistance development can be achieved by use of chitosan-arginine. Chitosan-arginine sensitizes bacteria to antibiotics with resistance and the mechanisms of resistance with chitosan-arginine appear to be overcome or futile. Hence there is no selective advantage to assume a resistant gene or express it. Therefore, chitosan-arginine will inhibit the development of resistance.

Example 2

Killing of Multi-Drug Resistant *Salmonella enterica* Serovar *typhumurium* with Chitosan-Arginine in Water Multi-drug resistant *Salmonella enterica* serovar *Typhimurium* strain DT104 (ATCC#700408) was tested for sensitivity to chitosan-arginine (C/A; Lot BC10; 25% functionalization, 43 kDa, 2.28 PDI, 88% DDA) in a standard bactericidal assay. Specifically, approximately $10^6$ bacteria/mL were resuspended in water alone or with chitosan-arginine concentrations of 25, 50, or 100 µg/mL in a total volume of 200 µL in a 96-well assay plate. The plate was left at room temperature for 24 hours then cells were centrifuged and resuspended in water, diluted, and plated to obtain surviving cfu.

Figure 2:
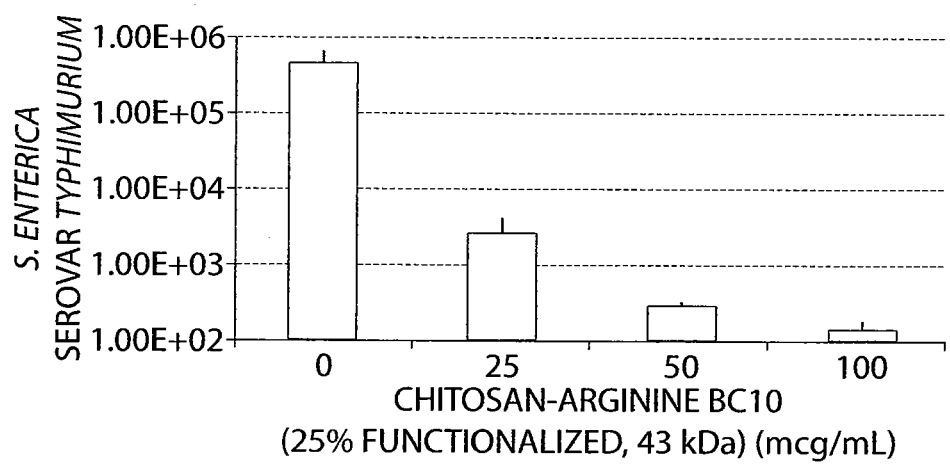
FIG. 2 depicts a bar graph showing the killing of Multi-drug resistant *Salmonella enterica* serovar *typhumurium* with chitosan-arginine in water over a course of 24 hours.

As shown in FIG. 2, chitosan-arginine inhibited the growth of Multi-drug resistant *Salmonella enterica* serovar *Typhimurium* strain DT104 (ATCC#700408) in water in a dose dependent manner.

Example 3

Killing of Methicillin-Resistant *Staphylococcus aureus* Clinical Isolates with Chitosan-Arginine

*S. aureus*, a Gram-positive species, has traditionally been a complication in battlefield injuries. While other pathogenic bacteria are beginning to emerge with similar activity, mupirocin and methicillin resistant *S. aureus* (MRSA) are increasingly disconcerting due to their increasing antibiotic resistance. Current treatments are expensive and utilize potentially toxic drugs with unsavory side effects such as colistin, imipenem-cilastatin and vancomycin for extended periods of time.

Figure 3:
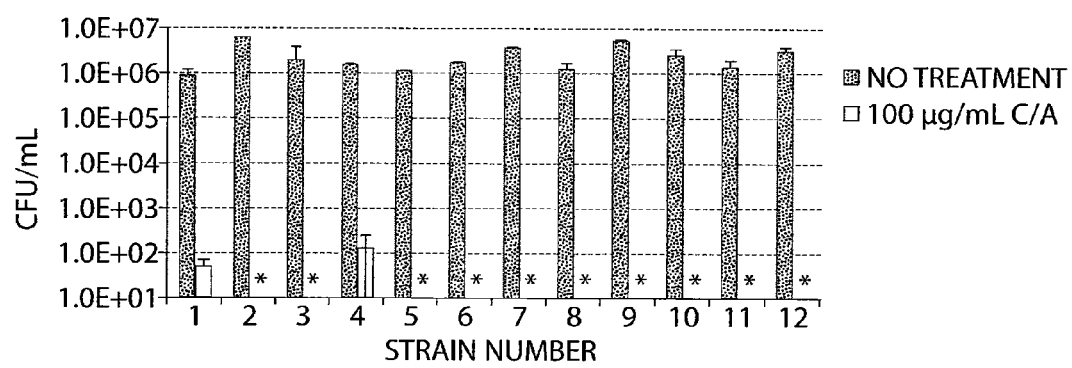
FIG. 3 depicts a bar graph showing the killing of clinical isolates of MRSA with 100 μg/mL chitosan-arginine. Asterisks (*) indicate complete sterilization of the bacteria where no CFU were found on the plate.

Twelve strains of clinical isolates were acquired from Providence Medical Center (Portland, Oreg.) to test the ability of chitosan-arginine to kill a variety of active MRSA strains. The MRSA were isolated from various sites of infection/colonization and included three each from the skin (strains 1-3), respiratory tract/sputum (strains 4-6), blood (strains 7-9), and nasal orifice (strains 10-12). In this brief study, a single concentration of 29 kDa, 38% functionalized chitosan-arginine (100 µg/mL) was used to treat approximately $10^6$ CFU/mL for 24 hours at room temperature. This dose was chosen because it is the lowest dose used for consistent and significant reductions of MRSA MW-2 in previous studies. The surviving and plated CFU/mL were measured are reported in FIG. 3. Note that chitosan-arginine is highly effective against clinical isolates of MRSA, essentially sterilizing the bacterial solutions in a day.

Additional studies were completed to assess the response of these Gram-positive bacteria MRSA to a dried layer of 29 kDa, 38% functionalized chitosan-arginine. In this test, a wound isolate of MRSA from Prof. Schlievert (University of Minnesota) was tested. Chitosan-arginine in a solution of 90% ethanol in water was deposited with varying surface coverage to polystyrene surfaces (12-well plate) and allowed to dry completely overnight.

Figure 4:
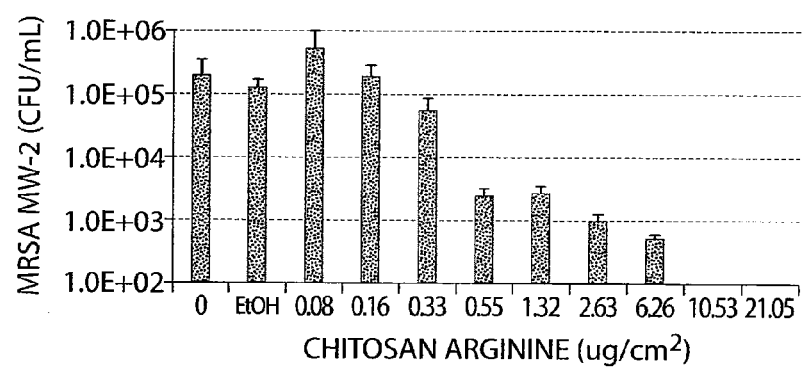
FIG. 4 depicts MRSA MW-2 dose response following 1-hour exposure to chitosan-arginine dried on polystyrene surface.

Subsequently, $1\times10^6$ bacteria of MRSA MW-2 were deposited on the surface and recovered after 1 hour. The surviving bacteria were plated and counted as shown in FIG. 4. Note that nearly complete sterilization is observed for surface densities less than 10 µg/cm².

Example 4

Killing of *Klebsiella pneumoniae* Laboratory and Multi-Drug Resistant Strains with Chitosan-Arginine

Figure 5:
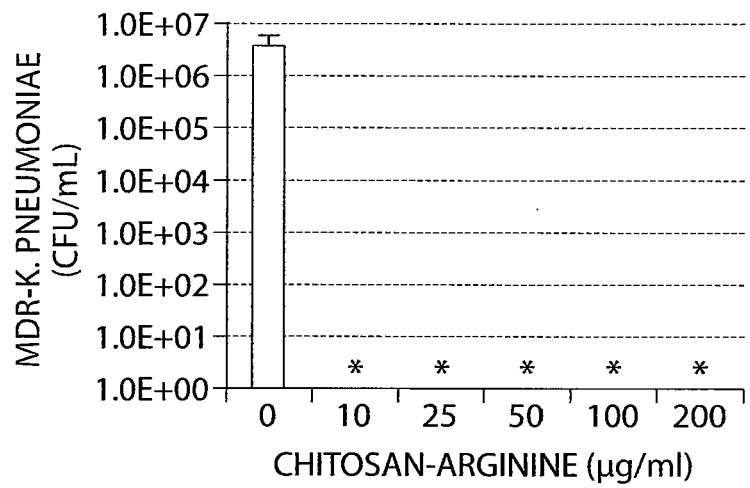
FIG. 5 depicts a bar graph showing the killing of *Klebsiella pneumoniae* multi-drug resistant strain (ATCC 70021) with chitosan-arginine.
Figure 6:
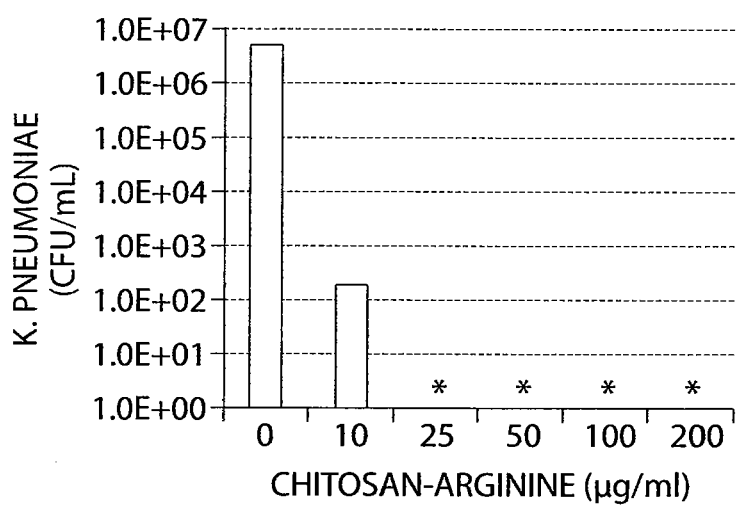
FIG. 6 depicts a bar graph showing the killing of *Klebsiella pneumoniae* strain (ATCC 13883) with chitosan-arginine.

*Klebsiella pneumoniae*, another Gram-negative species, has recently emerged as a highly drug resistant and lethal infective agent and is increasingly considered a threat for nosocomial infection. Two strains of *K. pneumoniae* were purchased from ATCC. The standard strain (ATCC 13883) has not developed any new resistance to known antibiotics. However, the multi-drug resistant strain (ATCC 70021) has known resistance to ampicillin, streptomycin, tetracycline, naladixic acid, ticarcillin, trimethoprim, sulfamethxazole, cefotaxime, and gentamicin. In each case, the *K. pneumoniae* were grown to densities of $\sim 5\times10^6$ bacteria/mL and treated with a dose of chitosan-arginine (52 kDa and 31% functionalized) in water from 0 to 100 µg/mL as shown in FIGS. 5 and 6 for four hours. The bacteria are spun down and the remaining bacteria reconstituted and plated on Agar plates to determine surviving colony forming units (CFU) per mL of original solution. The asterisk (*) in the figures indicates where no colonies were detected on the plate indicating complete sterilization of the bacteria.

In FIGS. 5 and 6, it is interesting to note that there is very little difference between the chitosan-arginine activity on the normal sensitive strain and the very multi-drug resistant strain of *K. pneumoniae*. The bactericidal mechanism of chitosan-arginine appears to be independent of the other resistance mechanisms utilized by this bacterium against a plethora of other antibiotics.

Example 5

*Acinetobacter baumannii* Multi-Drug Resistant Strains and Surface Treatments

*A. baumannii* is a Gram-negative bacillus that is naturally insensitive to a large number of antibiotics. Since 2003, there has been an increase in *A. baumannii* bloodstream infections in soldiers being treated at military hospitals. As an opportunistic pathogen, it is typically not a threat to healthy individuals, but can cause a variety of serious infections in compromised individuals, such as wounded soldiers. This bacterium is persistent on solid and dry surfaces, and is suspected of contaminating water and residing for months in dry soil.

Figure 7:
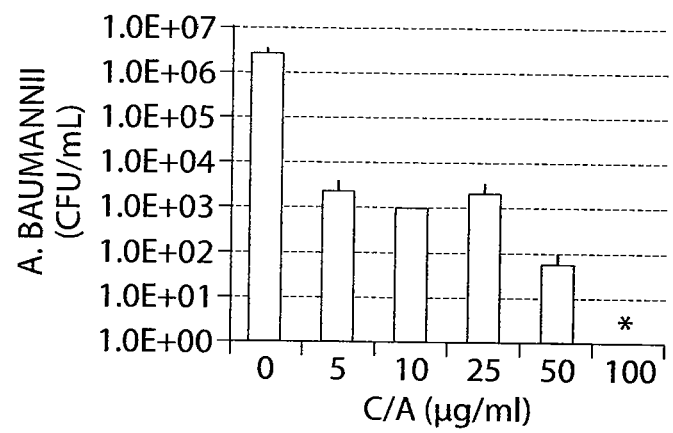
FIG. 7 depicts *A. baumannii* ATTC strain 19606 dose response to four hour treatments of chitosan-arginine.
Figure 8:
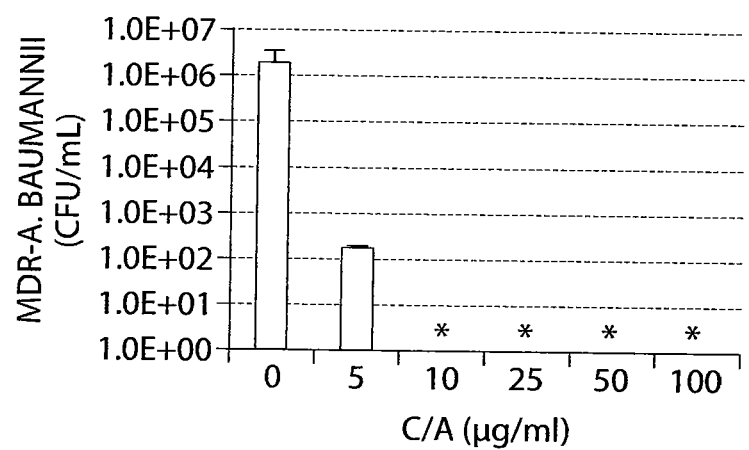
FIG. 8 depicts Multi-drug resistant *A. baumannii* ATTC strain BAA-1605 dose response to four hour treatments of chitosan arginine.

For these studies, two strains of *A. baumannii* were purchased from ATCC. The standard strain (ATCC 19606) has not developed any new resistance to known antibiotics. However, the multi-drug resistant strain (ATCC BAA-1605) has known resistance to ampicillin, tetracycline, naladixic acid, ticarcillin, trimethoprim, sulfamethoxazole, cefotaxime, ciprofloxacin, cefazolin cefazidime, cefuroxime, cefepime, imipenem, mezlocillin, piperacillin, gentamicin, and levofloxacin. Both strains were grown to densities of $\sim 5\times10^6$ bacteria/mL and treated with a dose of chitosan-arginine (52 kDA and 31% functionalized) in water from 0 to 100 µg/mL as shown in FIGS. 7 and 8 for four hours. The bacteria are spun down and the remaining bacteria reconstituted and plated on Agar plates to determine surviving colony forming units (CFU) per mL of original solution. The asterisk (*) in the figures indicates where no colonies were detected on the plate indicating complete sterilization of the bacteria. Note that the resistant *A. baumannii* is more sensitive to chitosan-arginine than the susceptible strain.

Example 6

Synergistic Reduction in Minimum Inhibitory Concentration (MIC) of an Antibacterial by Addition of Chitosan-Arginine The ability of chitosan-arginine to reduce MIC of an antibacterial was evaluated. The results are given for *Pseudomonas aeruginosa*, PA01, a type of Gram-negative bacteria that cause diseases that are typically treated by drugs e.g., Ciprofloxacin, Silver, Neomycin or Rifampicin.

A live/dead assay was used to determine synergy of chitosan-arginine with antibiotics silver, Ciprofloxacin, Rifampicin and Neomycin. The assay was conducted as follows. In each case, the minimum inhibitory concentration (MIC) in µg/ml was determined for the antibiotic alone against *Pseudomonas aeruginosa*. Subsequently, the MIC was determined for each of these antibiotics with the addition of small amounts of chitosan-arginine. The percent MIC of the pure material giving the same efficacy is plotted as a function of chitosan-arginine added. The addition of chitosan-arginine in all cases reduced the MIC dramatically, providing synergistic effects far less than its MIC of 8 µg/ml.

For example, in the raw data for the examination of synergistic effects of chitosan-arginine with Ciprofloxacin, the "checkerboard" plate shows simply where bacteria grow (dark stain) and where they are inhibited (clear well) as a function of added doses of Ciprofloxacin and chitosan-arginine.

The MIC data is summarized in Table 2. The MIC's of each of the antibiotics are shown at 0 µg/ml of added chitosan-arginine. While the addition of 4 µg/ml chitosan-arginine decreased the MIC of both Rifampicin and Neomycin by a factor at 16, the effect was even more dramatic for Ciprofloxacin and silver. The addition of 4 µg/ml chitosan-arginine to silver decreased its MIC by at least a factor of 40 and decreased the MIC of Ciprofloxacin by at least a factor of 80. Note that with the addition of 4 µg/ml of chitosan-arginine, the dose of Ciprofloxacin is still effective at 0.03 µg/ml, the lowest dose tested.

TABLE 2

Measured MIC's for each studied antibiotic in µg/ml in the absence or presence of various doses of chitosan-arginine
Reduction in Minimum Inhibitory Concentration (MIC) by chitosan-arginine (µg/ml)

| Chitosan-arginine added | Ciprofloxacin | Silver | Neomycin | Rifampicin |
| --- | --- | --- | --- | --- |
| 0 | 2 | 0.042 | 8 | 8 |
| 0.5 | 1 | 0.021 | 4 | 4 |
| 1 | 1 | 0.021 | 2 | 2 |
| 2 | .5 | 0.005 | 1 | 1 |
| 4 | 0.025* | 0.001* | 0.5 | 0.5 |

*Lowest value measured
The MIC of chitosan-arginine is 8 µg/mL.

Example 7

MW-2; Ciprofloxacin and Chitosan-Arginine Synergy

MW-2 is a wound clinical isolate of MRSA, a Gram-positive bacterium. A checkerboard assay for MIC at various ratios of chitosan-arginine and ciprofloxacin were tested to determine combinations of the two antibiotics that provided a minimum inhibitory concentration. Table 3 shows the resultant reductions in MIC from the MIC of the antibiotic alone. The FIC's indicate synergy or near synergy in all presented values.

TABLE 3

MW-2 Ciprofloxacin, chitosan-arginine synergy

| C/A concentration MIC = 16 µg/mL | Ciprofloxacin MIC = 4 µg/mL | FIC |
| --- | --- | --- |
| 8 | 0.03125 | 0.52 |
| 4 | 0.0625 | 0.27 |
| 2 | 0.5 | 0.25 |
| 1 | 1 | 0.31 |
| 0.25 | 2 | 0.52 |

C/A = chitosan-arginine

Example 8

Sensitization Observed

Sensitize MRSA (methicillin resistant *Staphylococcus aureus*) to Oxacillin
    Membrane targeting antibiotic
  Sensitize Mupirocin-Resistant MRSA to Mupirocin
    Inhibits protein synthesis
  Sensitize VRE (Vancomycin resistant *Enterococcus*) to Vancomycin
    Proteoglycan synthesis inhibitor limits cell wall growth
  Sensitize *E Coli* to chitosan-arginine with Ciprofloxacin
    Ciprofloxacin inhibits nucleic acid synthesis, chitosan-arginine is not very effective
  Sensitize Gentamicin resistant *Klebsiella pneumoniae* to Gentamicin
    Aminoglycosides inhibit protein synthesis by binding to portion of bacterial ribosome Sensitization results are summarized in Table 4. Three resistant bacteria are listed below with the drug to which they are resistant. The measured MIC is also listed. By definition, resistance is defined by a "resistance breakpoint" above which a bacterium is considered resistant (and is related to side effects and toxicity). The MIC of chitosan is also shown for these bacteria. The final column demonstrates the minimal amount of chitosan-arginine required to sensitize these bacteria, Gram-positive and Gram-negative, to the antibiotics to which they would be otherwise resistant.

TABLE 4 summary of tested resistant bacteria that are sensitized to antibiotics in the presence of chitosan-arginine

| Resistant bacteria (MIC in µg/mL) | Chitosan-arginine (µg/mL) | Antibiotic (µg/mL) | Antibiotic Resistance Breakpoint (µg/mL) |
| --- | --- | --- | --- |
| MRSA (>25) | 4 | 0.2 | 4 Oxacillin |
| MMRSA (>64) | 4 | 8 | 8 Mupirocin |
|  | 4 | 1 |  |
| VRE (>32) | 4 | 12.5 | 32 Vancomycin |
|  | 2 | 2 |  |
| *E. coli** (200) | 1 | 0.06 (Cipro) | Not defined Chitosan-arginine |
| *K. pneumoniae* (64) | 0.125 | 16 | 64 Gentamicin |
| *A. baumannii* (64) | 0.125 | 16 | 64 Gentamicin |

Example 9

Multi-Drug Resistant *Klebsiella pneumonaie* Gentamicin Sensitization with Chitosan-Arginine Broth microdilutions were performed for chitosan-arginine (31%, 52 kDa, 1.35 PDI, 89% DDA) and gentamicin in a minimal media, Freshwater Media, supplemented with 0.2% sodium succinate as a carbon source, and 0.1% casamino acids for Gram-positive strains. Approximately $10^5$ cells were added to each of the wells. The individual plates were incubated for 20 h at 37° C. Optical density readings of the plate were taken, and averaged to determine inhibited samples Inhibition is defined by the final optical density (OD) being less than or equal to ½ the control OD.

Figure 9:
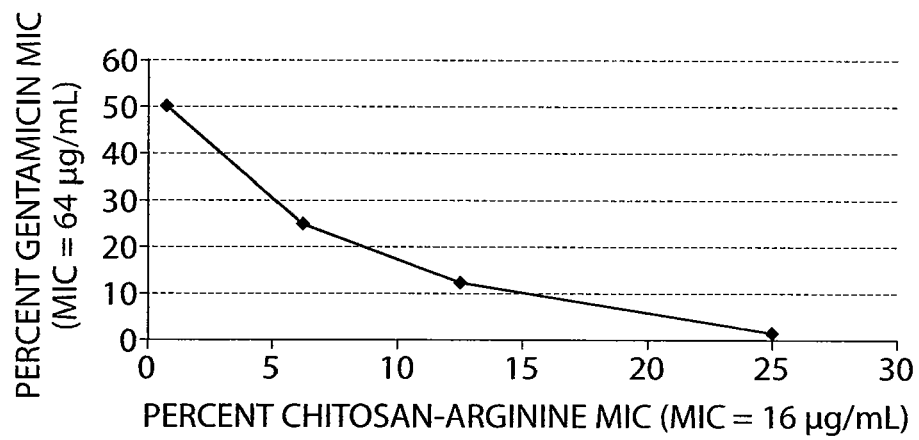
FIG. 9 depicts multi-drug resistant *Klebsiella pneumonaie* Gentamicin sensitization with chitosan-arginine.

The result for this assay is shown in FIG. 9.

Example 10

Sensitization Assay—Methicillin Resistant *Staphylococcus aureus* Oxacillin Sensitization Broth microdilutions were performed for chitosan-arginine (37%, 40 kDA, 2.45 PDI, 89% DDA) and oxacillin in a minimal media, Freshwater Media, supplemented with 0.2% sodium succinate as a carbon source, and 0.1% casamino acids for Gram-positive strains. Approximately $10^5$ cells were added to each of the wells. The individual plates were incubated for 20 h at 37° C. Optical density readings of the plate were taken, and averaged to determine inhibited samples Inhibition is defined by the final optical density (OD) being less than or equal to ½ the control OD.

Figure 10:
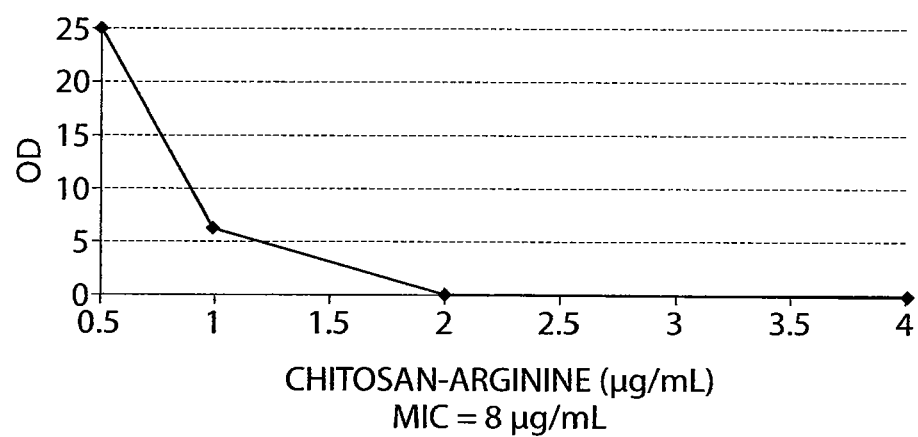
FIG. 10 depicts Methicillin resistant *Staphylococcus aureus* Oxacillin sensitization.

The result for this assay is shown in FIG. 10.

Example 11

Checkerboard Time Course Assay

Broth microdilutions were performed for chitosan-arginine (37%, 40 kDa, 2.45 PDI, 89% DDA) and Mupirocin in water. ~$10^6$ cells of Mupirocin and Methicilin resistant *Staphylcoccus aureus* (MMRSA, 2-4C strain from Washington University) was added to each of the wells. The plate was allowed to sit for 24 hours, before being centrifuged at 4000 RPM for 10 minutes, and resuspended in an appropriate enriched growth media (LB or Todd Hewitt Broth). The optical density of the plate was read over the course of 24 hours at 37° C. The optical density readings were used to compute a time to an arbitrary threshold of 0.25, which is correlated using a growth curve for this MMRSA, to virtual colony forming (vCFU) counts. Note that MMRSA is sensitive to mupirocin at 128 µg/mL. The addition of 4 µg/mL of chitosan-arginine to various doses of mupirocin reduces the vCFU by 4-5 orders of magnitude.

Figure 11:
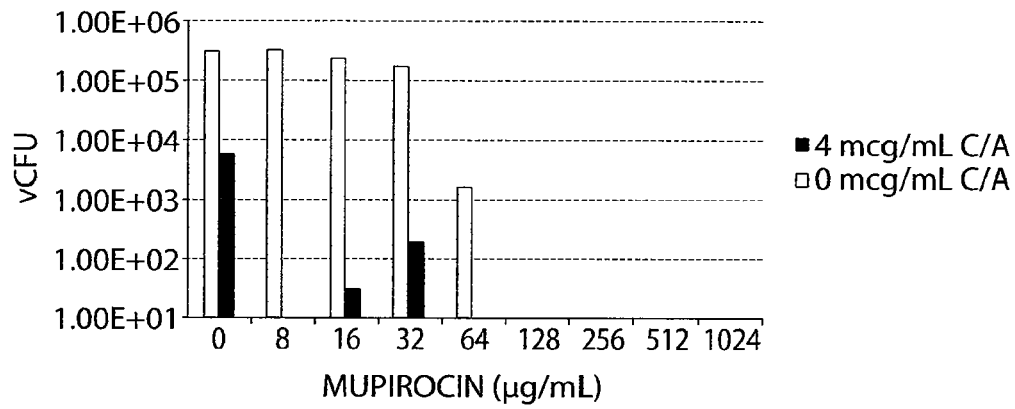
FIG. 11 depicts Mupirocin resistant MRSA 2-4C sensitization.

The result for this assay is shown in FIG. 11. Note that doses of Muipirocin below 64 to 128 µg/mL are ineffective antibacterials. However, the addition of 4 µg/mL chitosan-arginine sensitizes the MMRSA to Mupirocin doses as low at 8 µg/mL, well within the range of non-resistant bacteria.

Example 12

MMRSA Synergy Summary

Figure 12:
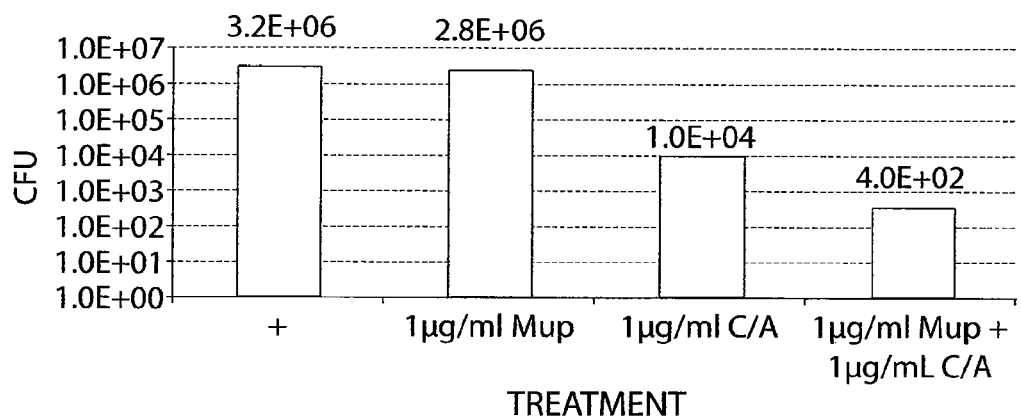
FIG. 12 depicts the MMRSA synergy results.

MMRSA synergy is summarized in FIG. 12. Note mupirocin is completely ineffective at 1 µg/mL while chitosan-arginine(37%, 40 kDa, 2.45 PDI, 89% DDA) alone reduces MMRSA viability by 2 logs. The combination of the two reduces the bacterial density from 3,200,000 to 400 CFU, a reduction of 4 logs. Chitosan-arginine sensitizes the MMRSA to Mupirocin.

Example 13

Chitosan-Arginine Synergy with Tobramycin Against *Pseudomonas aeruginosa*

A checkerboard assay was used to screen 64 unique combinations of chitosan-arginine (C/A; three different lots) and Tobramycin concentrations in triplicate against *P. aeuriginosa* strain PA01 (ATCC BAA-47). For each study, approximately $10^6$ cells per mL of chitosan-arginine compatible media (Freshwater succinate) were treated with different concentrations of chitosan-arginine (0.5-64 µg/mL) and/or different concentrations of tobramycin (0.031-4 µg/mL) in twofold serial dilutions. Bacteria were incubated at 37° C. for the standard 20 hours.

*P. aeuriginosa* produces the fluorescent pigment pyocyanin, which can be correlated with bacterial growth. Fluorescence was measured (485 nm excitation, 535 nm emission) and *P. aeruginosa* PAO1 MIC values obtained with this protocol are the same as those obtained using optical density (Hoffman, L. R.; D'Argenio, D. A.; MacCoss, M. J.; Zhang, Z.; Jones, R. A.; Miller, S. I. 2005 Aminoglycoside antibiotics induce bacterial biofilm formation. *Nature* 436, 1171-1175. The entire experiment was repeated three times.

As shown in Table 5, a synergistic effect as indicated by a FIC of <0.5, was observed when chitosan-arginine was used with Tobramycin to inhibit the growth of *P. aeuriginosa*.

TABLE 5

Chitosan-arginine synergy with Tobramycin

| C/A Treatment (MIC) µg/ml | Tobramycin (MIC) µg/ml | Tobramycin + C/A Treatment (µg/ml) | | | FIC |
|---|---|---|---|---|---|
| | | +0.125 | +0.063 | +0.031 | |
| C/A$^1$ (16) | (1) | 0.5 | 2 | 4 | ≤0.28 (S) |
| C/A$^2$ (32) | (0.5) | 0.5 | 2 | 4 | ≤0.27 (S) |
| C/A$^3$ (32) | (0.5) | 0.5 | 4 | 8 | ≤0.30 (S) |

$^1$27%, 32 kDa, PDI, % DDA;
$^2$31%, 54 kDa, PDI, % DDA;
$^3$25%, 43 kD, 2.28 PDI, 88% DDA

Example 14

Chitosan-Arginine Synergy with Ciprofloxacin

A modified checkerboard assay was used to screen 4 unique combinations of chitosan-arginine (C/A; 25% Functionalization, 43 kDa, 2.28 PDI, 88% DDA) and Ciprofloxacin concentrations, as well as alone (6 replicates) against *E. coli* O157:H7 (ATCC 700728).

Approximately $10^6$ cells per mL of Mueller Hinton media were treated with different concentrations of chitosan-arginine (100 or 50 µg/mL) and/or different concentrations of Ciprofloxacin (0.1 or 0.05 µg/mL). Bacteria were incubated at 37° C. and the OD595 was monitored at 5 minute intervals for 18 hours to compare the rate of growth over time between treatments.

Synergistic slow release killing of *E. coli* O157:H7 (ATCC 700728) was observed when chitosan-arginine was used together with Ciprofloxacin.

Example 15

Chitosan-Arginine Synergy with Oxacillin Against MRSA Strain MW-2 (ATCC BAA-1707) in PBS Micro-dilutions were performed for chitosan-arginine (C/A; 25% Functionalization, 43 kDa, 2.28 PDI, 88% DDA) and Oxacillin to cover a range of doses in 96-well plates in a checkerboard assay format. Approximately $10^6$ cells/mL were added to each well. Incubation occurred at ambient temperature for 20 h, then bacteria were centrifuged and resuspended in an appropriate growth media. The optical density (OD) was read over the course of 18 h at 37° C. The time (in seconds) to an arbitrary threshold OD of 0.15 was used with reference to a growth curve, to calculate the initial bacterial concentration of bacteria (vCFU). Synergy is defined as >2 log decrease in the vCFU with combination treatment at 24 hours compared with that of the more active of each of the two treatments alone. In this experiment, chitosan-argine has a bactericidal concentration at 8 µg/mL, and oxacillin has bactericidal concentration at >6.25 µg/mL.

As shown in Table 6, a synergistic and sensitizing effect was observed when chitosan-arginine was used with oxacillin to inhibit the growth of MRSA strain MW-2 (ATCC BAA-1707).

TABLE 6

Chitosan-arginine synergy and sensitization with Oxacillin against MRSA strain MW-2 (ATCC BAA-1707) in PBS

| Assay | Treatment (µg/mL) | Total logs recoverable | C/A (log reduction alone) | Oxacillin (log reduction alone) | Total log reduction | Log reduction beyond C/A |
|---|---|---|---|---|---|---|
| 1* | C/A 2 Oxa 3.1 | 5.0 | 0.05 | 1.3 | 4.6 | 3.3 |
|  | C/A 4 Oxa 3.1 | 5.0 | 0.10 | 1.3 | 4.3 | 3.5 |
|  | C/A 8 Oxa 3.1 | 5.0 | 0.68 | 1.3 | 4.3 | 3.7 |

*Chitosan-arginine 25% Functionalization, 43 kDa, 2.28 PDI, 88% DDA

Example 16

Chitosan-Arginine and Oxacillin Synergy Against MRSA Strain MW-2 (ATCC BAA-1707) Standard Checkerboard Assay in Mueller Hinton Media A checkerboard assay was used to screen 64 unique combinations of chitosan-arginine (C/A) and Oxacillin concentrations in triplicate against MRSA strain MW-2 (ATCC BAA-1707). For each study, approximately $10^6$ cells per mL of Mueller Hinton broth were treated with concentrations of C/A (0.5-64 µg/mL) and/or concentrations of Oxacillin (0.5-64 µg/mL) in two-fold serial dilutions. Bacteria were incubated at 37° C. for the standard 20 hours. MRSA MIC values were obtained by OD595 (optical density). The entire experiment was repeated three times.

As shown in Table 7, a synergistic effect was observed when chitosan-arginine was used with Oxacillin to inhibit the growth of MRSA Strain MW-2 (ATCC BAA-1707) in Mueller Hinton media.

TABLE 7

Chitosan-arginine and Oxacillin synergy against MRSA Strain MW-2 (ATCC BAA-1707) standard checkerboard assay in Mueller Hinton media

| Treatment (µg/mL) | MIC of Oxa with C/A | MIC of Oxa alone (µg/mL) | MIC of C/A with Oxa | MIC of C/A alone (µg/mL) | FIC |
|---|---|---|---|---|---|
| C/A 8 Oxa 1 | 1 | 4 | 8 | 32 | 0.5 |

* Chitosan-arginine 25% Funct, 43 kDa, 2.28 PDI, 88% DDA

Example 17

Chitosan-Arginine Synergy with Tetracycline Against *E. coli* O157:H7 (ATCC 700728)

Micro-dilutions were performed for chitosan-arginine (C/A) and Tetracycline to cover a range of doses in 96-well plates in a checkerboard assay format. Approximately $10^6$ cells/mL were added to each well. Incubation occurred at ambient temperature for 20 h, then bacteria were centrifuged and resuspended in an appropriate growth media. The optical density (OD) was read over the course of 18 h at 37° C. The time (in seconds) to an arbitrary threshold OD of 0.15 was used with reference to a growth curve, to calculate the initial bacterial concentration of bacteria (vCFU). Synergy is defined as >2 log decrease in the vCFU with combination treatment at 24 hours compared with that of the more active of each of the two treatments alone. In this experiment, chitosan-argine has a bactericidal concentration at 8 µg/mL, and Tetracycline has bactericidal concentration at >6.25 µg/mL.

As shown in Table 8, a synergistic effect was observed when chitosan-arginine was used with Tetracycline to inhibit the growth of *E. coli* O157:H7 (ATCC 700728).

TABLE 8

Chitosan-arginine synergy with Tetracycline against *E. coli* O157:H7 (ATCC 700728)

| Assay | Treatment (µg/mL) | Total logs recoverable | C/A (log reduction alone) | Tetracycline (log reduction alone) | Total log reduction | Log reduction beyond C/A |
|---|---|---|---|---|---|---|
| 1* | C/A 2 TET 3.1 | 5.0 | 0.05 | 1.3 | 4.6 | 3.3 |
|  | C/A 4 TET 3.1 | 5.0 | 0.10 | 1.3 | 4.3 | 3.5 |
|  | C/A 8 TET 3.1 | 5.0 | 0.68 | 1.3 | 4.3 | 3.7 |

In another experiment, micro-dilutions in chitosan-arginine (C/A) compatible media (Freshwater succinate) were performed for chitosan-arginine and Tetracycline to cover a range of doses in 96-well plates in a checkerboard assay format. Approximately $10^6$ cells/mL were added to each well. Incubation occurred at 37° C. for 24 h and the optical density (OD) at 595 nm was read. The OD was used to determine the MIC at each concentration and control. Fractional Inhibitory Concentration (FIC) was calculated to determine if synergy occurred.

Representative results are shown in Table 9. FIC values of <0.5 were observed in ranges from 1-16 µg/mL of chitosan-arginine and 0.004-0.125 µg/mL of Tetracycline.

TABLE 9

FIC values showing chitosan-arginine synergy with Tetracycline against *E. coli* O157:H7 (ATCC 700728)

| Treatment (µg/mL) | MIC of TET with C/A | MIC of TET alone (µg/mL) | MIC of C/A with TET | MIC of C/A alone (µg/mL) | FIC |
|---|---|---|---|---|---|
| C/A 1 TET 0.063 | 0.063 | 0.5 | 1 | 32 | 0.16 |
| C/A 2 TET 0.031 | 0.031 | 0.5 | 2 | 32 | 0.13 |
| C/A 4 TET 0.016 | 0.016 | 0.5 | 4 | 32 | 0.16 |
| C/A 4 TET 0.008 | 0.008 | 0.5 | 4 | 32 | 0.14 |
| C/A 4 TET 0.004 | 0.004 | 0.5 | 4 | 32 | 0.13 |

*C/A 31% Functionalization, 53 kDa, 1.35 PDI, 89% DDA

Example 18

Chitosan-Arginine Synergy with Hydrogen Peroxide ($H_2O_2$) Against MRSA Strain MW-2 (ATCC BAA-1707) in Water The experiment was performed as described in Example 11 except that $H_2O_2$ was used instead of oxacillin.

As shown in Table 10, a synergistic effect was observed when chitosan-arginine was used with $H_2O_2$ to inhibit the growth of MRSA strain MW-2 (ATCC BAA-1707) in water.

TABLE 10

Chitosan-arginine and $H_2O_2$ synergy against MRSA strain MW-2 (ATCC BAA-1707) in water

| Log reduction from the most active agent | | C/A µg/mL | | |
|---|---|---|---|---|
| | | 8 | 4 | 2 |
| $H_2O_2$ % | 0.0028 | 4.6 | 3.8 | 5.0 |
| | 0.0014 | 3.4 | 2.6 | 4.1 |
| | 0.0007 | 1.4 | 1.5 | 3.7 |

*C/A 25% Functionalization, 43 kDa, 2.28 PDI, 88% DDA

Example 19

Chitosan-Arginine Synergy with Hydrogen Peroxide ($H_2O_2$) Against *P. aeuriginosa* strain PA01 (ATCC BAA-47) in Water The experiment was performed as described in Example 18 except that *P. aeuriginosa* strain PA01 (ATCC BAA-47) was tested instead of MRSA.

As shown in Table 11, a synergistic effect was observed when chitosan-arginine was used with $H_2O_2$ to inhibit the growth of *P. aeuriginosa* strain PA01 (ATCC BAA-47) in water.

TABLE 11

Chitosan-arginine and $H_2O_2$ synergy against *P. aeuriginosa* strain PA01 (ATCC BAA-47) in water

| Log reduction from the most active agent | | Chitosan-arginine Dose in micrograms/mL | |
|---|---|---|---|
| | | 16 | 8 |
| $H_2O_2$ % | 0.0014 | 3.4 | 3.3 |
| | 0.0007 | 0.0 | 2.8 |

*C/A 25% Functionalization, 43 kDa, 2.28 PDI, 88% DDA

Example 20

Chitosan-Arginine Synergy with Hydrogen Peroxide ($H_2O_2$) Against Vanomycin Resistant *Enterococcus faecalis* (ATCC 51299) in PBS The experiment was performed as described in Example 11 except that Vanomycin resistant *Enterococcus faecalis* (ATCC 51299) was tested instead of MRSA and $H_2O_2$ was used instead of Oxacillin.

As shown in Table 12, a synergistic effect was observed when chitosan-arginine was used with $H_2O_2$ to inhibit the growth of Vanomycin resistant *Enterococcus faecalis* (ATCC 51299) in PBS.

TABLE 12

Chitosan-arginine and $H_2O_2$ synergy against Vanomycin resistant *Enterococcus faecalis* (ATCC 51299) in PBS

| Log reduction from the most active agent | | C/A µg/mL | |
|---|---|---|---|
| | | 16 | 8 |
| $H_2O_2$ % | 0.0014 | 1.4 | 1.3 |
| | 0.0007 | 0.0 | 3.0 |

*C/A 25% Functionalization, 43 kDa, 2.28 PDI, 88% DDA

Example 21

Chitosan-Arginine Synergy with Hydrogen Peroxide ($H_2O_2$) Against *E. coli* O157:H7 (ATCC 700728) in PBS The experiment was performed as described in Example 11 except that *E. coli* O157:H7 (ATCC 700728) was tested instead of MRSA and $H_2O_2$ was used instead of Oxacillin.

As shown in Table 13, a synergistic effect was observed when chitosan-arginine was used with $H_2O_2$ to inhibit the growth of *E. coli* O157:H7 (ATCC 700728) in PBS.

TABLE 13

Chitosan-arginine and $H_2O_2$ synergy against *E. coli* O157:H7 (ATCC 700728) in PBS

| Log reduction from the most active agent | | C/A µg/mL | |
|---|---|---|---|
| | | 16 | 8 |
| $H_2O_2$ % | 0.0014 | 3.2 | 3.2 |
| | 0.0007 | 0.1 | 0.8 |

*C/A 25% Functionalization, 43 kDa, 2.28 PDI, 88% DDA

Example 22

MRSA Strain MW-2 (ATCC BAA-1707) Oxacillin Sensitization

A time-kill assay was performed to optimize the range of antimicrobial concentrations. Specifically, broth micro-dilutions were performed for chitosan-arginine (C/A; 37% functionalization, 40 kDa) and Oxacillin in water in 96-well plates. $10^6$ cells were added to each well. Incubation occurred at room temperature for 20 h, then the bacteria were centrifuged and resuspended in an appropriate growth media. The optical density (OD) was read over the course of 18 h at 37° C. The time (in seconds) to an arbitrary threshold OD of 0.25 was used with reference to a growth curve, to calculate the initial bacterial concentration of bacteria (vCFU).

Figure 13:
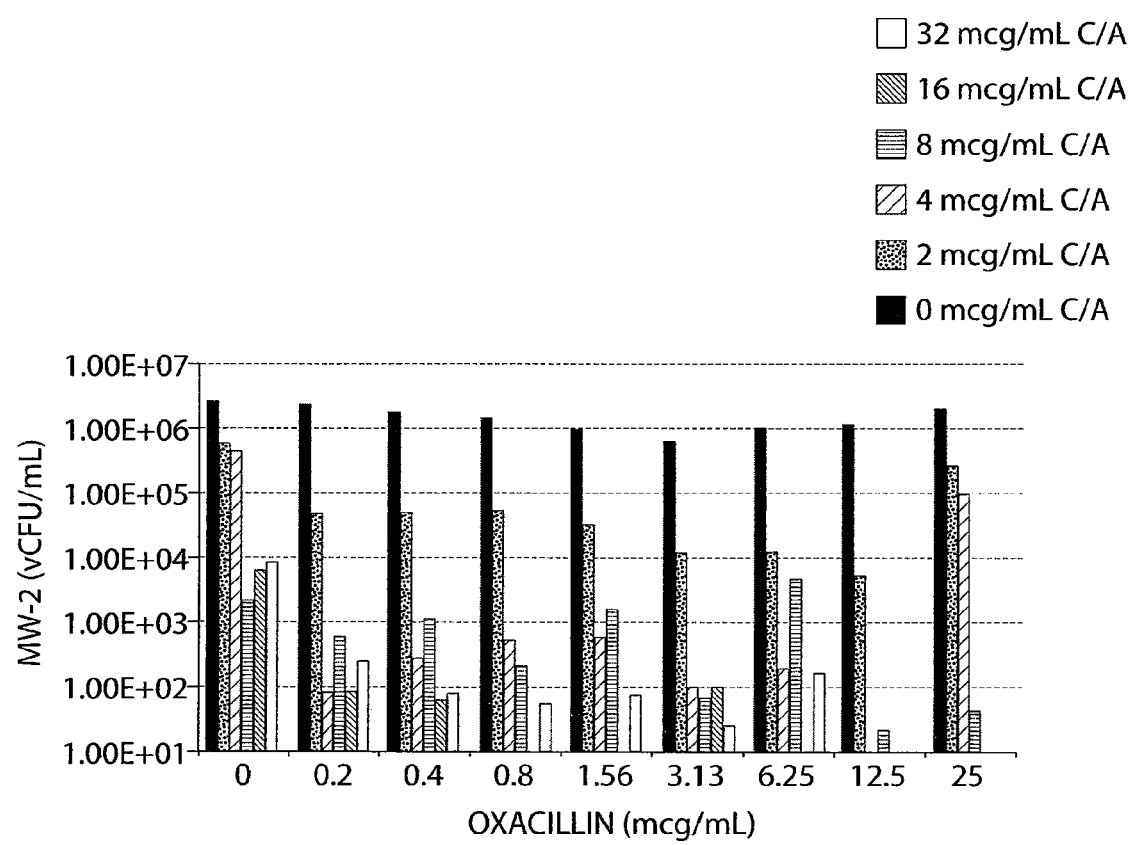
FIG. 13 depicts the results of the Time-Kill assay used to optimize the range of chitosan-arginine and Oxacillin concentrations.

The results are shown in FIG. 13.

Example 23

Chitosan-Arginine/Oxacillin Checkerboard Growth Inhibition Assays Against MRSA Strain MW-2 (ATCC BAA-1707)

Figure 14A:
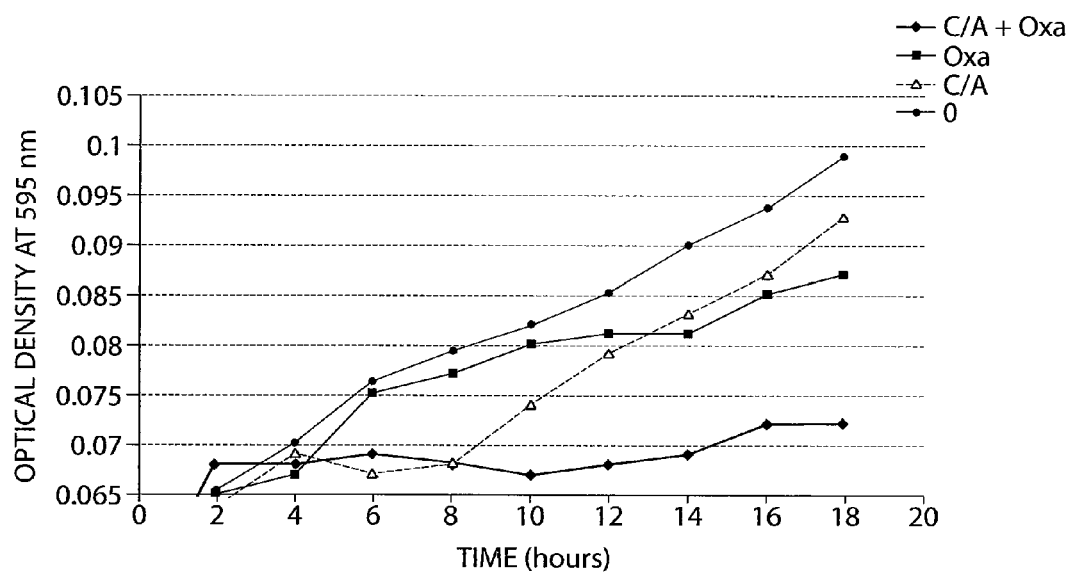
FIG. 14A depicts the time course of growth inhibition of MRSA strain MW-2 (ATCC BAA-1707) by chitosan-arginine and Oxacillin.

Broth micro-dilutions were performed for chitosan-arginine (C/A; 37% Functionalization, 40 kDa) and Oxacillin, in a chitosan-arginine compatible media. Approximately $10^5$ cells was added to each of the wells. The optical density of the plate was read over the course of 24 hours at 37° C. As shown in the growth curves in FIG. 14A, chitosan-arginine (1 µg/mL) sensitized the inhibition of MRSA strain MW-2 (ATCC BAA-1707) by Oxacillin (0.78 µg/mL). Neither antimicrobial alone had a significant an effect on growth of the bacteria.

Figure 14B:
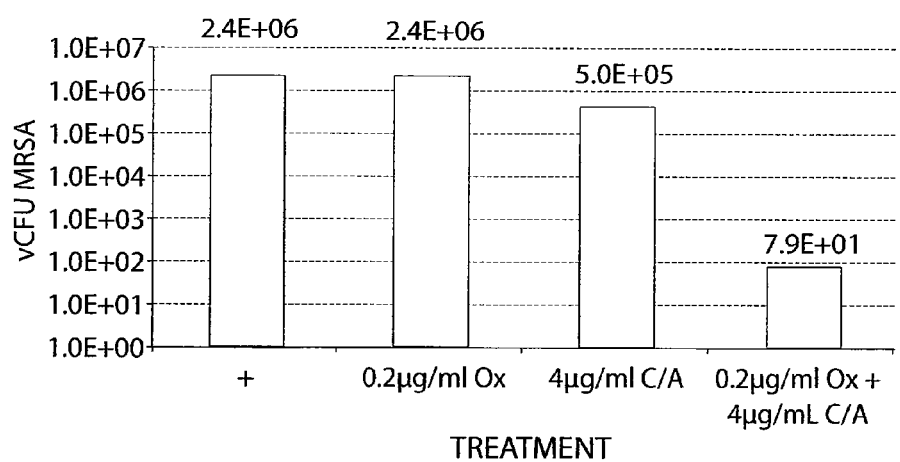
FIG. 14B depicts a bar graph showing the bactericidal synergy of chitosan-arginine and oxacilling on MRSA strain MW-2 (ATCC BAA-1707).

Similarly, chitosan-arginine (4 µg/mL) was able to sensitize the inhibition of MRSA strain MW-2 (ATCC BAA-1707) by Oxacillin (0.2 µg/mL), as shown in FIG. 14B by the 4 log increase in bactericidal activity of the combination of treatments over the most effective individual component.

Example 24

Summary of Sensitization of Resistant Bacteria to Antibiotics by Chitosan-Arginine As shown in Table 14, chitosan-arginine reduces the MIC of the resistant bacteria to well below the breakpoint, thus sensitizing the bacteria to the antibiotic to which they have become resistant. Measured MIC in column 1 clearly shows resistance defined by antibiotic resistance breakpoint in column 4. All experiments were performed with 24 hour treatment of antimicrobials (standard MIC).

TABLE 14

Sensitization summary

| Resistant bacteria (MIC in µg/mL) | Chitosan-arginine (µg/mL) | Antibiotic (µg/mL) | Antibiotic Resistance Breakpoint (µg/mL) |
|---|---|---|---|
| MRSA (>25) | 4 | 0.2 | 4 Oxacillin |
| MMRSA (>64) | 4 | 8 | 8 Mupirocin |
| | 4 | 1 | |
| VRE (>32) | 4 | 12.5 | 32 Vancomycin |
| | 2 | 2 | |
| *E. coli** (200) | 1 | 0.06 (Cipro) | Not defined Chitosan-arginine |
| *K. pneumoniae* (64) | 0.125 | 16 | 64 Gentamicin |
| *A. baumannii* (64) | 0.125 | 16 | 64 Gentamicin |

Example 25

Minimum Inhibitory Concentration (MIC) Studies

Minimum Inhibitory Concentrations (MIC) were obtained using the broth microdilution antibacterial susceptibility method in Mueler Hinton broth. Approximately $10^5$ cells was added to each well in 96-well plate containing 2-fold dilutions of chitosan-arginine starting from 256 µg/mL (8 replicates per treatment). The individual plates were incubated for 20 hours at 37° C. Optical density readings of the plate were taken, and averaged to determine inhibited samples as no visible growth.

The results for Gram-negative and Gram-positive bacteria are shown in Tables 15A and 15B, respectively.

TABLE 15A

MIC (µg/mL) of chitosan for selected Gram-negative bacteria in Fresh Water media (FW) or Meuler Hinton broth (MH), (— indicates not measured)

| Species | Strain | ATCC # | MIC C/A in FW | MIC C/A in MH |
|---|---|---|---|---|
| Escherichia coli | 0157:H7 | 700728 | 8 | >256 |
| Pseudomonas aeruginosa | PA01 | BAA-47 | 32 | >256 |
| Pseudomonas aeruginosa | AMT 0032-4 | Seattle Hospital, WA | — | 128 |
| Pseudomonas aeruginosa | PA MDR MR 7 | Seattle Hospital, WA | — | 4 |
| Shewanella putrefaciens | | 8071 | — | 16 |

TABLE 15B

MIC (µg/mL) of chitosan-arginine for selected Gram-positive bacteria

| Species | Strain | MIC C/A MH (FW) |
|---|---|---|
| Staphylococcus aureus | MW-2 | 32 (8) |
| Bacillus subtilis | ATCC 23857 | 16 |
| Staphylococcus aureus | MNDON | 16 |
| Staphylococcus aureus | MNHOCH | 64 |
| Staphylococcus aureus | Clinical Isolate MRSA #1 | 16 |
| Staphylococcus aureus | Clinical Isolate MRSA #2 | 16 |
| Staphylococcus aureus | Clinical Isolate MRSA #3 | 16 |
| Staphylococcus aureus | Clinical Isolate MRSA #4 | 16 |
| Staphylococcus aureus | Clinical Isolate MRSA #5 | 16 |
| Staphylococcus aureus | Clinical Isolate MRSA #6 | 32 |
| Staphylococcus aureus | Clinical Isolate MRSA #7 | 16 |
| Staphylococcus aureus | Clinical Isolate MRSA #8 | 16 |
| Staphylococcus aureus | Clinical Isolate MRSA #9 | 16 |
| Staphylococcus aureus | Clinical Isolate MRSA #10 | 32 |
| Staphylococcus aureus | Clinical Isolate MRSA #11 | 16 |
| Staphylococcus aureus | Clinical Isolate MRSA #12 | 16 |
| Staphylococcus epidermidis | Sepi | 16 |
| Staphylococcus aureus | Isolate 2-1A | 32 |
| Staphylococcus aureus | Isolate 2-4C | 32 |
| Staphylococcus aureus | Isolate 2-9A | 16 |
| Listeria monocytogenes | ATCC51414 | 32 |
| Listeria monocytogenes | ATCC 19115 | 16 |
| Staphylococcus aureus | 6538 | 32 |

Other embodiments are within the following claims.

What is claimed is:

1. A method of inhibiting the growth of a bacterium or killing a bacterium in a subject, comprising contacting the bacterium with a derivatized chitosan and an anti-bacterial agent in an effective combined amount, thereby inhibiting the growth of the bacterium or killing a bacterium, wherein the anti-bacterial agent and the derivatized chitosan are present at a concentrations, or administered at doses, which result in a fractional inhibitory concentration (FIC) of less than or equal to 0.5, wherein the derivatized chitosan comprises a chitosan of the following formula (I):

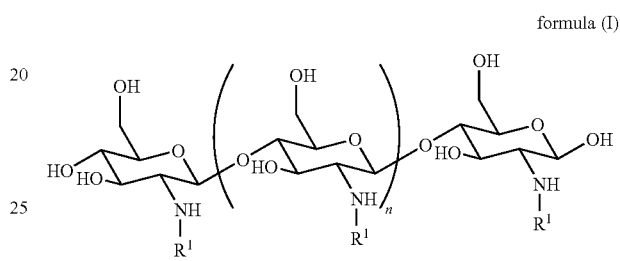

formula (I)

wherein:

n is an integer between 20 and 6000; and each $R^1$ is independently selected for each occurrence from hydrogen, acetyl,

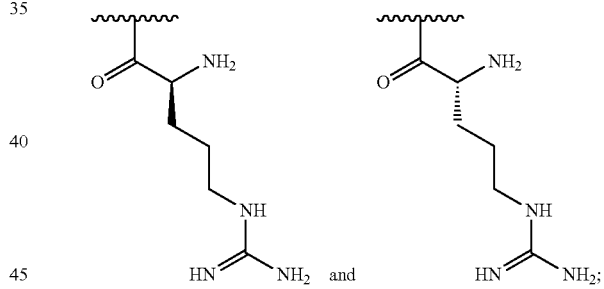

wherein at least 25% of $R^1$ substituents are H, at least 1% of $R^1$ substituents are acetyl, and at least 2% of $R^1$ substituents are

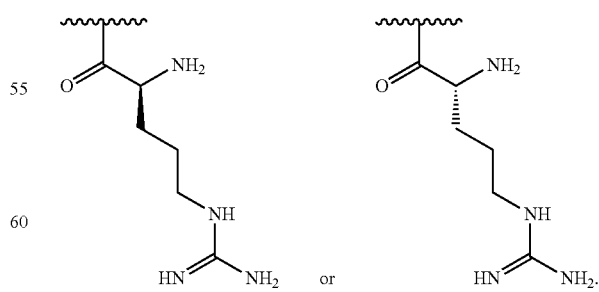

2. The method of claim 1, wherein the inhibition is at least 2 times greater than the sum of the inhibition seen with either the anti-bacterial agent or the derivatized chitosan used alone.

3. The method of claim 1, wherein the bacterium is resistant to the derivatized chitosan when the derivatized chitosan is administered without the anti-bacterial agent.

4. The method of claim 1, wherein the anti-bacterial agent is present at a concentration, or administered at a dose, which would not result in inhibition of bacterial growth or killing the bacterium in the absence of the derivatized chitosan.

5. The method of claim 1, wherein the derivatized chitosan is present at a concentration, or administered at a dose, which would not result in inhibition of bacterial growth or killing the bacterium in the absence of the anti-bacterial agent.

6. The method of claim 1, wherein the anti-bacterial agent and derivatized chitosan are present at a concentration, or administered at a dose, which result in a bactericidal activity at least 2 logs more effective than the most effective activity in the absence of the chitosan derivative or anti-bacterial agent.

7. The method of claim 1, wherein the anti-bacterial agent is selected from aminoglycosides; beta-lactam antibiotics; macrolides; antibiotic polypeptides; antibiotic lipopeptides; antibiotic glycopeptides; monobactams; quinolones; sulfonamides; and tetracyclines, and the bacterium is selected from Gram-positive and Gram-negative bacterium.

8. The method of claim 1, wherein the anti-bacterial agent is selected from Ciprofloxacin, Rifampicin, Neomycin, silver and Gentamicin, and the bacterium is *Pseudomonas aeruginosa*.

9. The method of claim 1, wherein the anti-bacterial agent is present at less than 8 μg/ml.

10. The method of claim 1, wherein the derivatized chitosan is present at less than 16 μg/ml.

11. The method of claim 10, wherein the derivatized chitosan is present at less than 8 μg/ml.

12. The method of claim 1, wherein the molecular weight of the derivatized chitosan is from 25 to 100 kDa.

13. The method of claim 12, wherein the molecular weight of the derivatized chitosan is from 20 to 30 kDa.

14. The method of claim 1, wherein the polydispersity index of the derivatized chitosan is from 1.0 to 2.5.

15. The method of claim 1, wherein the derivatized chitosan is functionalized at between 5% and 50%.

* * * * *